US007002697B2

(12) United States Patent
Domash et al.

(10) Patent No.: US 7,002,697 B2
(45) Date of Patent: Feb. 21, 2006

(54) TUNABLE OPTICAL INSTRUMENTS

(75) Inventors: Lawrence H. Domash, Conway, MA (US); Adam M. Payne, Conway, MA (US); Eugene Y. Ma, Brookline, MA (US); Nikolay Nemchuk, North Andover, MA (US); Ming Wu, Princeton, NJ (US); Robert Murano, Malden, MA (US); Steven Sherman, Arlington, MA (US); Matthias Wagner, Boston, MA (US)

(73) Assignee: Aegis Semiconductor, Inc., Woburn, MA (US)

( * ) Notice: Subject to any disclaimer, the term of this patent is extended or adjusted under 35 U.S.C. 154(b) by 109 days.

(21) Appl. No.: 10/211,970

(22) Filed: Aug. 2, 2002

(65) Prior Publication Data

US 2003/0072009 A1 Apr. 17, 2003

Related U.S. Application Data

(60) Provisional application No. 60/309,704, filed on Aug. 2, 2001, provisional application No. 60/310,047, filed on Aug. 4, 2001, provisional application No. 60/322,208, filed on Sep. 14, 2001, provisional application No. 60/335,178, filed on Nov. 28, 2001, provisional application No. 60/386,973, filed on Jun. 6, 2002, provisional application No. 60/394,500, filed on Jul. 9, 2002.

(51) Int. Cl.
*G01B 9/02* (2006.01)
(52) U.S. Cl. .................................................. 356/519
(58) Field of Classification Search ................ 356/454, 356/519, 521; 372/32
See application file for complete search history.

(56) References Cited

U.S. PATENT DOCUMENTS

| | | | |
|---|---|---|---|
| 4,885,622 A | 12/1989 | Uchiyama et al. | ............. 357/30 |
| 5,162,239 A | 11/1992 | Winer et al. | .................... 437/4 |
| 5,185,272 A | 2/1993 | Makiuchi et al. | ............... 437/5 |
| 5,387,974 A * | 2/1995 | Nakatani | .................... 356/519 |

(Continued)

FOREIGN PATENT DOCUMENTS

DE 44 24 717 A1 1/1996

(Continued)

OTHER PUBLICATIONS

Baumeister, P., "Simulation of a rugate filter via a stepped-index dielectric multilayer", Applied Optics, vol. 25, No. 16, 1986, pp. 2644-2645.

(Continued)

*Primary Examiner*—Gregory J. Toatley, Jr.
*Assistant Examiner*—Michael A. Lyons
(74) *Attorney, Agent, or Firm*—Wilmer Cutler Pickering Hale and Dorr LLP

(57) ABSTRACT

An optical instrument including: a thermo-optically tunable, thin film, free-space interference filter having a tunable passband which functions as a wavelength selector, the filter including a sequence of alternating layers of amorphous silicon and a dielectric material deposited one on top of the other and forming a Fabry-Perot cavity structure having: a first multi-layer thin film interference structure forming a first mirror; a thin-film spacer layer deposited on top of the first multi-layer interference structure, the thin-film spacer layer made of amorphous silicon; and a second multi-layer thin film interference structure deposited on top of the thin-film spacer layer and forming a second mirror; a lens for coupling an optical beam into the filter; an optical detector for receiving the optical beam after the optical beam has interacted with the interference filter; and circuitry for heating the thermo-optically tunable interference filter to control a location of the passband.

20 Claims, 22 Drawing Sheets

U.S. PATENT DOCUMENTS

| | | | |
|---|---|---|---|
| 5,408,319 A | 4/1995 | Halbout et al. | 356/352 |
| 5,528,071 A | 6/1996 | Russell et al. | 257/458 |
| 5,539,848 A | 7/1996 | Galloway | 385/89 |
| 5,599,403 A | 2/1997 | Kariya et al. | 136/258 |
| 5,742,630 A | 4/1998 | Jiang et al. | 372/50 |
| 5,751,757 A | 5/1998 | Jiang et al. | 372/50 |
| 5,767,712 A | 6/1998 | Takemae et al. | 327/152 |
| 5,790,255 A | 8/1998 | Jackson et al. | 356/375 |
| 5,942,050 A | 8/1999 | Green et al. | 136/258 |
| 5,953,355 A | 9/1999 | Kicly et al. | 372/43 |
| 6,037,644 A | 3/2000 | Daghighian et al. | 257/444 |
| 6,075,647 A | 6/2000 | Braun et al. | 359/578 |
| 6,091,504 A * | 7/2000 | Walker et al. | 356/437 |
| 2002/0105652 A1 | 8/2002 | Domash et al. | 356/481 |
| 2002/0145139 A1 | 10/2002 | Wagner et al. | 257/53 |
| 2002/0185588 A1 | 12/2002 | Wagner et al. | 250/214.1 |

FOREIGN PATENT DOCUMENTS

| | | | |
|---|---|---|---|
| DE | 4424717 | 1/1996 | |
| EP | 0125390 | 2/1984 | 29/66 |
| EP | 0139487 | 5/1985 | 21/203 |
| EP | 0178148 | 4/1986 | 31/10 |
| EP | 0559347 | 9/1993 | 31/224 |
| EP | 0773640 | 5/1997 | |
| EP | 0860885 | 8/1998 | 31/36 |
| EP | 0883194 | 12/1998 | 31/105 |
| EP | 0899835 | 3/1999 | 3/25 |
| EP | 0899836 | 3/1999 | 3/25 |
| JP | 60210826 | 10/1985 | 31/4 |
| JP | 07168040 | 7/1995 | 6/122 |
| JP | 08250551 | 9/1996 | 21/60 |
| WO | WO 99/30394 | 6/1999 | 3/25 |
| WO | WO 00/13350 | 3/2000 | |
| WO | WO 00/23838 | 4/2000 | |
| WO | WO 01/16637 | 5/2001 | |
| WO | WO 01/67646 | 9/2001 | |
| WO | WO 01/73850 | 10/2001 | |

OTHER PUBLICATIONS

Fernandes, M. et al., "VIS/NIR detector based on $\mu$c-Si:H p-l-n structures", Thin Solid Films, Elsevier Science S.A., vol. 364, No. 1-2, Mar. 2000, pp. 204-208.

Kobayashi, Y. et al., "Improvement on Coupling Efficiency for Passive Alignment of Stacked Multi-Fiber Tapes to a Vertical-Cavity Surface-Emitting Laser Array", Extended Abstracts of the 1996 International Conference on Solid Devices and Materials, 1996, pp. 655-657.

Li, H., "Refractive Index of Silicon and Germaninum and Its Wavelength and Temperature Derivatives", J. Phys. and Chem. Ref. Data, vol. 9, 1980, p. 561.

Wipiejewski, T. et al., "Vertical-Cavity Surface-Emittng Laser Diodes for Short Distance Optical Fiber Networks", Proceeding of the Electronic Components and Technology Conference, Washington D.C., IEEE vol. 44, 1994, pp. 330-334.

Niemi T et al., "Tunable Silicon Etalon for Simultaneous Spectral Filtering and Wavelength Monitoring of a DWDM Transmitter", *IEEE: Photonics Technology Letters*, vol. 13, No. 1, Jan. 2001, pp. 58-60.

Hohlfeld, et al., "Thermally Tunable Optical Filter Array", *Proc. of SPIE*, (2003), vol. 4989, pp. 143-154.

Hohlfeld, et al., "A Thermally Tunable, Silicon-Based Optical Filter", *Sensor and Actuators*, (2003), vol. 103, pp. 93-99.

* cited by examiner

TUNABLE OPTICAL INSTRUMENTS

RELATED APPLICATIONS

This application claims domestic priority under 35 U.S.C. §119(e) to provisional U.S. patent applications having Ser. Nos. 60/309,704 (filed Aug. 2, 2001), 60/310,047 (filed Aug. 4, 2001), 60/322,208 (filed Sep. 14, 2001), 60/335,178 (filed Nov. 28, 2001), 60/386,973 (filed Jun. 6, 2002); and 60/394,500 (filed Jul. 9, 2002), all incorporated herein by reference.

BACKGROUND OF THE INVENTION

Tunable optical instruments are a class of instruments in which a property of light, such as power level, is measured at more than one wavelength. Such instruments include optical spectrum analyzers (OSAs), optical channel monitors (OCMs) and others used in the wavelength division multiplexed (WDM) optical communication field, as well as other fields.

An OSA is a piece of equipment or a measurement instrument that receives an optical input and produces an output that represents the optical power contained in the optical input over a range of wavelengths. When we use the term "optical," we mean to refer to a band of wavelengths of electromagnetic radiation including at least visible light, ultraviolet (UV) and infrared (IR). The tern should be viewed inclusively, particularly when an application of the described technology overlaps one of the explicitly named bands and also includes wavelengths marginally outside those bands.

Like all instruments realized in the "real world," OSAs have a finite resolution determined by characteristics of the components of which they are constructed. However, spectrum analysis is generally thought of as producing a continuous representation of the power distribution across the measured band. That is, the power at each wavelength within the measured band is represented, even though resolution limits may mean that the represented power actually includes some power from nearby wavelengths, as well.

In some optical communication systems, plural channels of information may be transmitted on a single medium by modulating each channel onto a carrier having a different wavelength. Such systems include wavelength division multiplexed (WDM) systems. An instrument adapted to measure optical power at the specific, discrete channel carrier wavelengths is an OCM. Of particular, but not exclusive, interest to us are WDM systems operating with channel carrier wavelengths around 1500 nm.

Conventional OSAs and OCMs are bulky and expensive because the tunable filters used employ mechanical tuning means, such as moving a grating, stretching a fiber, etc. Such systems are also slow to tune, often requiring seconds to tune just a few nanometers in wavelength.

SUMMARY OF THE INVENTION

According to aspects of embodiments of the invention, there are provided several systems and variations thereon.

An optical instrument may include a tunable free-space filter as a wavelength selector. A free-space filter is defined as one for which light is propagated normal to the planar surface of the filter in the form of a beam, as contrasted with devices that guide light in waveguides or fibers. The optical instrument may be an optical spectrum analyzer (OSA). Indeed, the OSA may be constructed and arranged as an optical channel monitor for wavelength-division multiplexed optical communication systems.

According to some variations, the tunable free-space filter is a tunable thin film filter (TTFF). The TTFF may be thermo-optically tunable. The tunable filter may be a multi-layer film structure incorporating thin film semiconductor materials. The temperature, and hence the wavelength, of the TTFF may be varied using an external thermal energy transfer device. The thermal energy transfer device may be a resistive heating device. The resistive heating device may be a ring-shaped metallic film, defining an aperture through which light passes through the filter. The resistive heating device may alternatively be an optically transparent layer that is integrated with the filter in a location such that light passes through the resistive heating device. In one set of variants, the transparent layer may be a transparent conducting oxide. Alternatively, the transparent layer may be a doped thin film selected from the list including amorphous, micro-crystalline, and polycrystalline semiconductor films, or it may be a doped crystalline semiconductor.

Various TTFF structures are possible. The TTFF may have a single-cavity Fabry-Perot structure or may have a multi-cavity structure.

Packaging variants can be made. For example, the TTFF and the optical detector can be mounted in a single hermetic package. The single hermetic package may be a TO-style package. Within the single hermetic package may be one or more discrete temperature sensors. Also, within the single hermetic package may be one or more temperature-stabilizing devices.

Several calibration aids can be included. The optical instrument may further include an external source of one or more known wavelength signals. Alternatively, the instrument may include an internal source of one or more known wavelength signals. In yet another alternative, the instrument may further comprise passive interferometric structures within the optical instrument that create a stable wavelength reference. In this alternative, the interferometric structures may include a substrate of the tunable free-space filter. The interferometric structure may interact with a known light source to establish a reference signal.

The optical instrument may further include a device that measures temperature of the thermo-optically tunable TTFF to determine wavelength. The device that measures the temperature may be integrated with the TTFF. The TTFF may further include a heater layer. In that case, the heater layer may further include the device that measures the temperature. For example, the device that measures the temperature may monitor resistance of the heater layer. In one variant where the device that measures the temperature monitors the resistance of the heater layer, there is a source of a DC current to heat the heater layer and a source of a superposed AC current that is sufficient to monitor resistance of the heater layer.

The optical instrument may further comprise a detector having an output and a signal processor connected to receive a signal from the detector output, the signal processor converting the signal received from the detector output to power v. wavelength data.

In yet another packaging variant, the optical instrument may include an electronics module; an optical detector; a fiber optic input; and a transistor outline (TO) package into which are mounted the tunable free-space filter, the optical detector and the fiber optic input, the TO package including pins through which electrical connections between the tunable free-space filter and the optical detector, and the electronics module are made. In this instance, the instrument may further include a single enclosure supporting the TO package and the electronics module.

BRIEF DESCRIPTION OF THE DRAWINGS

In the drawings in which like reference designations indicate like elements.

DETAILED DESCRIPTION

The present invention will be better understood upon reading the following detailed description of various aspect of embodiments thereof in connection with the figures.

Tunable thin film filters (TTFFs) are free-space filters that admit beams of light, for example collimated light, and filter out specific wavelength or sets of wavelengths for transmission or reflection. The optical beams to be filtered are unguided except for input and output optics which extract them and insert them into waveguides such as optical fibers.

Figure 1:
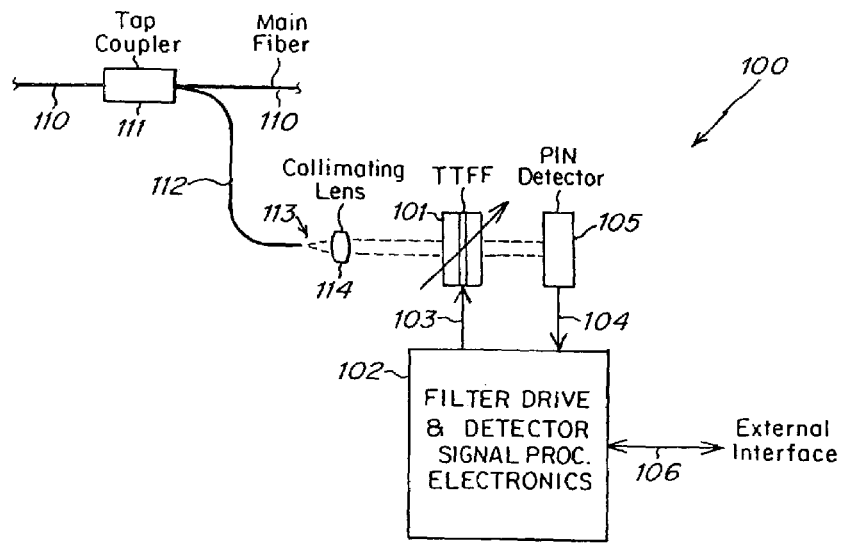
FIG. 1 is a schematic block diagram of an optical instrument including a TTFF.

A block diagram of an optical instrument 100 including a TTFF 101, such as an OSA or OCM is shown in FIG. 1. The TTFF 101 comprises semiconductor thin films possessing large thermo-optic coefficients leading to wide tunability with no moving parts. Integral with or closely associated with the TTFF 101 are devices for heating and/or cooling the filter over a wide temperature range. A signal-carrying optical fiber 110 passes through a top coupler 111. Some of the signal is carried in fiber 112 to the instrument 100. The signal exits the fiber at 113 to pass through a collimating lens 114 to TTFF 101. The control electronics 102 sweep the TTFF 101 through a range of wavelengths by controlling the current drive 103 to a resistive heater. The TTFF 101 can alternatively be tuned to a specific wavelength. Either during the wavelength sweep, or when the TTFF wavelength has stabilized, depending on the type of measurement, a photocurrent 104 from a PIN detector 105 is read. The resulting information is processed as appropriate, and then the system conveys the resulting spectrum or measurement to the outside world 106. In an OSA application, the result is a table of power measurements over the continuous range of wavelengths through which the TTFF has been swept. In a simple OCM application, the result communicated is a "channel power table" which is simply a list of power measurements at each of the discrete carrier wavelengths or channels in use or available in an optical communication system.

The internal functions of OSAs and OCMs have been described in multiple previous patents and publications. We will focus on those aspects that are specific to the use of a TTFF in such instruments.

Figure 2:
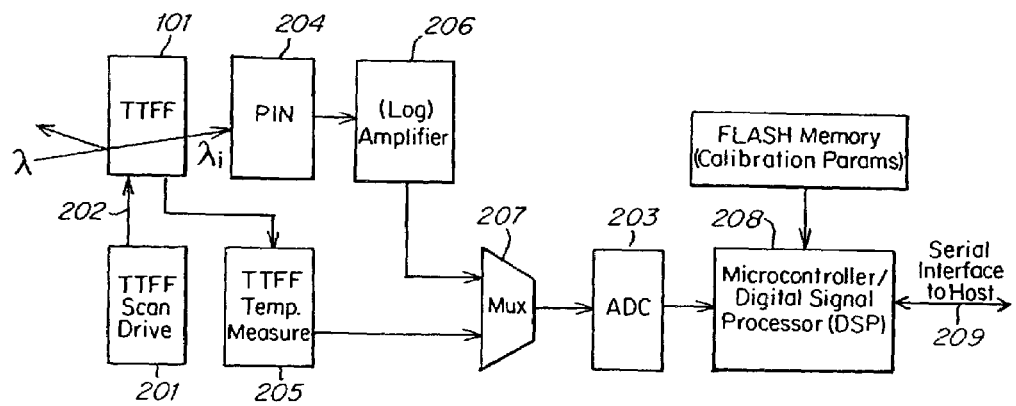
FIG. 2 is a block diagram of the instrument of FIG. 1, further detailing signal processing aspects thereof.

As one example, an embodiment of an OSA or OCM built using the TTFF is shown in FIG. 2. An analog circuit 201 periodically drives the tunable thin film heater with a pulse of current 202 that rapidly heats the filter 101, thereby shifting its transmission to a wavelength beyond the range to be scanned. Either during the heating pulse or as the TTFF cools, an analog-to-digital converter 203 samples alternately the PIN photodiode 204 output and a signal from a film temperature measurement circuit 205 that represents the temperature of the active film. The PIN photodiode 204 output may be amplified, for example by log amplifier 206. A multiplexer 207 selects between the PIN photodiode output and the temperature measurement output. Once converted to the digital domain, the results are fed to a microprocessor or digital signal processor 208. DSPs are available with built-in A/D converters and full-function interfaces thus integrating into one component several of the functions just described. The signal is then processed to produce the output spectrum or carrier table, as described above. Finally, the results are communicated to the host system through a standard serial interface 209.

Next, we discuss producing and measuring the temperature swing described above, as well as controlling the temperature of a thermally tunable filter. The quality of the temperature control scheme will ultimately determine many performance parameters of the filter, including tuning speed, tuning range, peak width, and power consumption. When choosing a temperature control method, heating and cooling speed and efficiency, temperature uniformity, and material properties all need to be considered.

Heating and cooling elements for a thin-film filter can be classified into three categories based on their proximity to the active layer. The first category includes heating/cooling elements external to the device, thermally coupled to its substrate or package. A second category includes heating or cooling elements integrated into the device, providing more efficient thermal control due to the increased proximity to the active layer. The third, highly efficient, thermal design uses the active layer itself as the heating or cooling element.

An external temperature controller is one simple way to control the temperature of a thermally tunable device. For example, the filter can be mounted on a feedback-controlled thermo-electric (T/E) heater/cooler. This approach is simple but has many disadvantages. First, a T/E heater/cooler has a limited temperature range—translating into limited tuning range, and is relatively slow to perform large temperature swings, on the order of seconds to tune through a complete range, thus defeating one of the advantages of TTFFs, namely their small thermal mass. Also, because the T/E element is external to the device itself, the substrate and the package will be heating and cooled along with the device. This contributes to relatively large power consumption and slower temperature control and tuning speed by increasing the thermal mass of the system.

Figure 3:
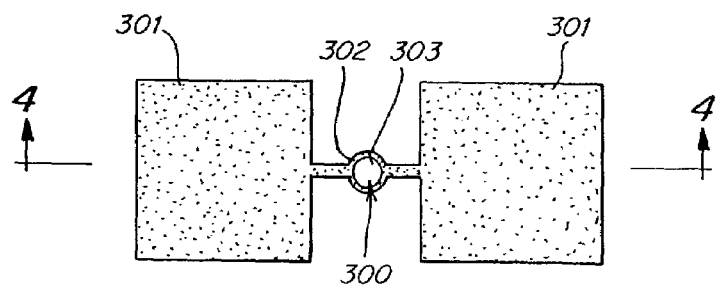
FIG. 3 is a plan view of a tunable Fabry-Perot filter having a ring heater.
Figure 4:
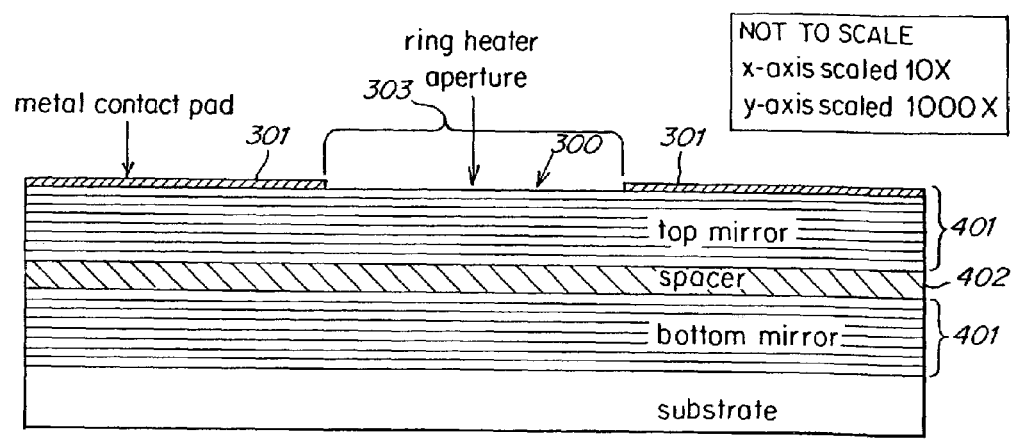
FIG. 4 is a schematic cross section view of the filter of FIG. 3.

To solve these problems, a resistive heating element can be integrated directly with the filter. One embodiment of a tunable thin-film Fabry-Perot filter is shown in FIG. 3. Metal pads 301 make electrical contact to a thin-film metallic ring-shaped resistor 302, which heats the filter 300. In the cross-sectional view of FIG. 4, 401 indicates the dielectric thin-film mirror stacks of a Fabry-Perot filter. The Fabry-Perot cavity layer 402 is the thermally tunable material.

By running a current through the resistive heater 302 using contact pads 301, resistive heat is generated, which will change the optical properties of the cavity layer 402, as well as other layers, and thus tune the filter 300. Light travels perpendicular to the page in FIG. 3, through the hole 303 at the center of the resistive heater, the active filter area. This type of heater could be made of any suitable material capable of carrying enough current to generate the necessary resistive heat. For example, a ring-shaped heater 302 with a 300 micron diameter, 50 microns wide, leaving a 200 micron aperture 303, made of a 100 nm thick film of chromium would have a resistance of approximately 10 Ohm. The power dissipated by such a resistive heater is given by $P=I^2R$. Assuming 1 mW is needed to heat the filter sufficiently to have the desired tuning range, a voltage of 3.2 V across the heating element would be generate 0.32 mA and 1 mW of power. This device can be mounted on a heat sink attached to a T/E cooler held at a constant, low temperature, which would provide cooling. Thus, using the pulse drive noted above, a temperature sawtooth, and hence a wavelength sawtooth, results.

This method of heating is more efficient than the external heater described above because the heating element is in closer proximity to the active layer. This will lead to faster heating and tuning, and less power consumption. Also, a heating element of this type has no temperature range independent of the operating temperature limits of the material of the TTFF and the conductive ring, itself. However, the disadvantage of this configuration is poor temperature uniformity across the active filter's area because heat must be transferred from the inner edge of the heater to the center of the active filter area. This non-uniform temperature distribution will lead to a broad or distorted transmission peak because the beam occupies a finite, non-zero area of the active filter area, and therefore will be distributed across a range of different filter properties corresponding to different local temperatures.

Figure 5:
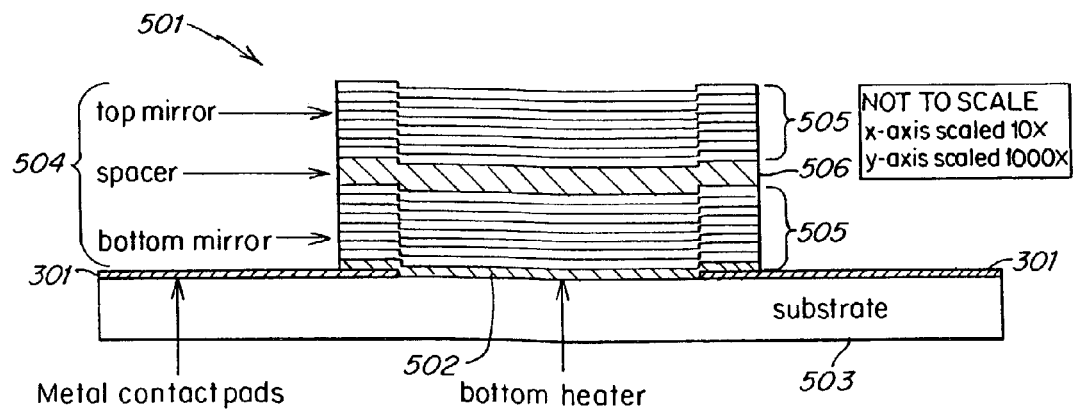
FIG. 5 is a schematic cross section view of a filter having a bottom heater.

According to another arrangement, a thin-film resistive heater is made transparent to the wavelengths of interest. In this case, it could be positioned in the path of the light, providing more uniform heating. FIG. 5 shows a tunable thin-film Fabry-Perot 501 filter with this type of heating element 502 integrated between the substrate 503 and filter stack 504. Such a heating element 502 could alternatively be one of the mirror stack layers 505 or even the Fabry-Perot cavity layer 506, if such are arranged to be both transparent to the wavelength of use and also sufficiently conductive. While the films currently in use for filters in the wavelength division multiplying (WDM) industry are primarily dielectrics, an advantage of our semiconductor thin films is that they combine good optical properties and low loss with desired thermo-optic properties and good conductivity when suitably doped. A heating element 502 of this type for application in the telecommunications industry could be made of one of several transparent conductors, such as zinc oxide, indium tin oxide, a doped thin film of amorphous, microcrystalline, or poly-crystalline semiconductor, etc. Poly-silicon films, formed by re-crystallizing in an oven films deposited as amorphous silicon, are especially adaptable to this purpose. Because these transparent conductors have higher resistivities than most pure metals, the heating element should be made as small as possible to maximize the resistive power density.

One other possible material for a semi-transparent resistive heater is a doped crystalline silicon or some other semiconductor crystal. In this case, the filter substrate would be the crystalline semiconductor wafer, and the filter would be fabricated on top of a doped area. Of course, the semiconductor both intrinsic and doped, must be transparent to the wavelengths of interest.

The doped semiconductor, and the thin-film transparent resistive heaters both greatly improve the temperature uniformity across the filter over the ring-shaped resistive heater described above. Also, the filter and heater combination can be made smaller leading to lower power consumption and a small device footprint.

Figure 6:
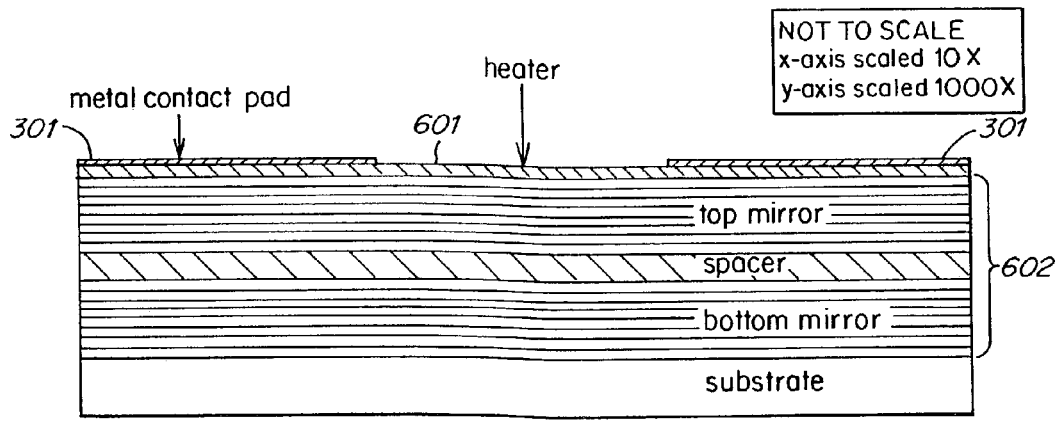
FIG. 6 is a schematic cross section view of a filter having a top heater.
Figure 7:
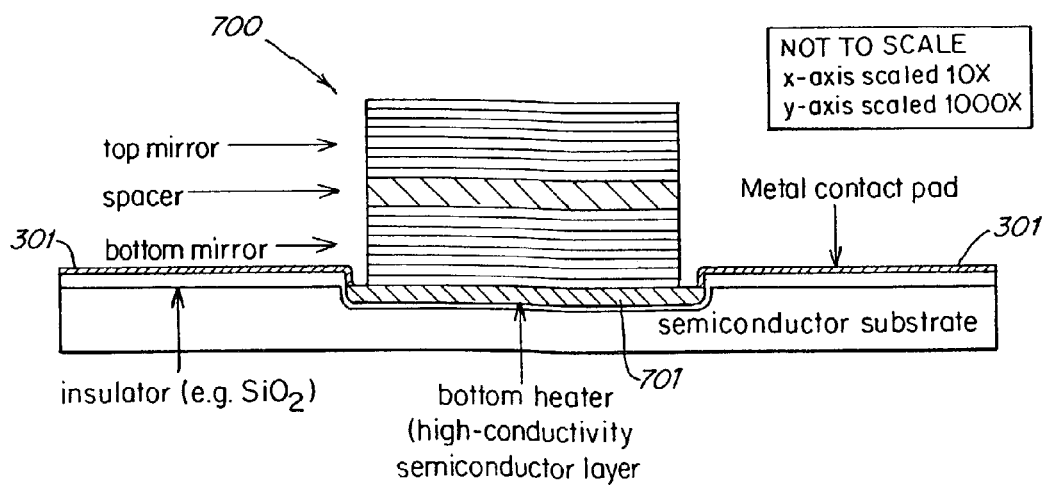
FIG. 7 is a schematic cross section view of a filter having a bottom crystalline semiconductor heater.
Figure 8:
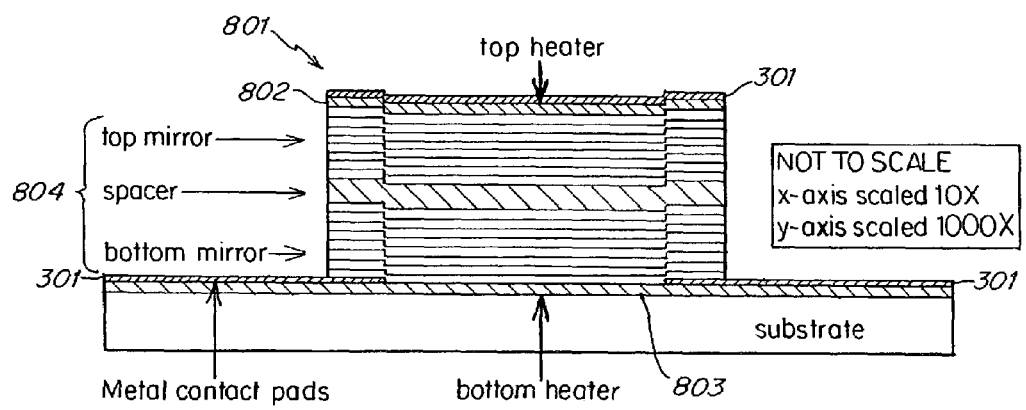
FIG. 8 is a schematic cross section view of a filter having both a top heater and a bottom heater in the same filter structure.

FIG. 6 shows the heating element 601 integrated on top of the filter stack 602. FIG. 7 shows a filter 700 fabricated on top of a doped area 701 of a crystalline semiconductor. The doped area 701 forms a heater element. FIG. 8 shows a filter 801 with a transparent thin-film resistive heating element fabricated on the top 802 and the bottom 803 of the filter stack 804.

An advantage of having two heating elements is double the heating capability. Also, one of the elements could be used as a thermometer provided it is made of a material whose resistance is a function of temperature. The choice of configuration depends on the specific application requirements.

All the integrated resistive heating element designs considered above have the advantages of uniform temperature distribution over the filter area, relatively close proximity to the tunable layer, and no inherent temperature limit. However, because the heating element is in the path of the light, it may absorb or scatter light leading to a smaller transmission peak and a higher insertion loss of the filter. Also, many of the transparent conducting oxides that might be used for this purpose are not stable with temperature. Finally, these configurations are not the most efficient ways to heat the tunable layer. For example, for the configuration shown in FIG. 5, much of the heat generated by the heating element 502 is lost to the substrate 503 instead of going directly to the tunable layer 506.

Figure 9:
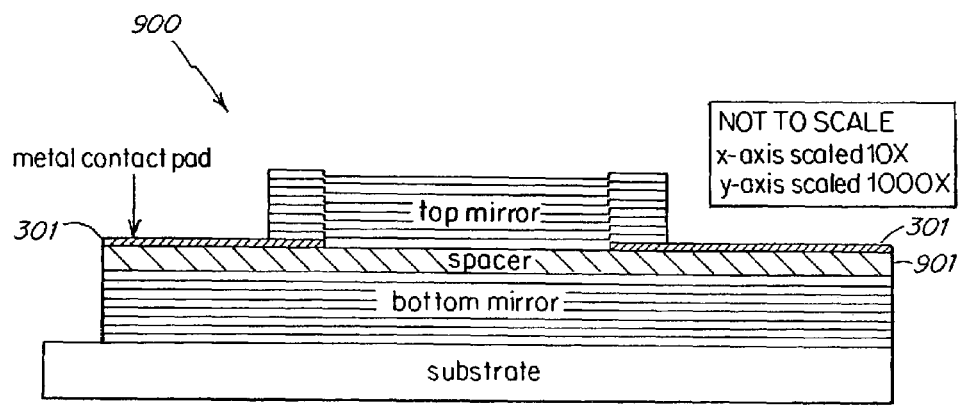
FIG. 9 is a schematic cross section view of a filter in which the spacer layer also serves as the heater.

The most efficient way to heat the tunable layer is to use the layer itself as the heating element, as briefly noted above, provided it is electrically conductive, for example a doped semiconductor thin film. FIG. 9 shows a tunable Fabry-Perot filter 900 with electrical contact 301 directly to the tunable layer 901, which is used as a resistive heater in the same way as described above for the integrated heater. Of course in this case, the tunable layer 901 must have a low enough resistivity to be able to carry enough current to generate the necessary resistive heat, in addition to meeting all the optical requirements of a Fabry-Perot cavity layer.

This configuration involves the fewest compromises in terms of the heater and tuning performance. Since the tunable layer itself is the heating element, no more efficient heating of that layer is possible, meaning the fastest tuning time and lowest power consumption. Also, as with the transparent integrated heating elements described above, relatively uniform heating can be achieved. Lastly with this configuration, no additional layers are in the path of the light traveling through the Fabry-Perot filter. Therefore there will be no unnecessary loss or modification to the optical signal. For a spacer having an index of 3.5, tuning over 30 nm in the 1500 nm band requires a temperature change of more than 350 C. Such a large local heating is achieved in our embodiments by a combination of concentrated electrical power dissipation in a microscopic volume, extremely strong film adhesion and materials where properties are stable under repeated cycling.

Consider now a spacer material with a thermo-optic coefficient $dn/dT=2\times10^{-4}/°$ C. used in the above-described structure.

To get a sense of the materials properties requirements, we let the length L and width W of the heater element be L=W=1 mm and set the operation voltage to be 10V. The power density is $P/WL=I^2R/WL=V^2/RWL$, and should be about 1 W/Cm$^2$. Therefore the target heater film resistance R must be about 10K ohm. For a thin film heater layer thickness d=100 nm and W/L=1, then the target resistivity of the heater material needs to be RdW/L=0.1 ohm-cm.

Materials that can be used for the heater must have not only low optical absorption at the wavelengths of interest ($\approx$1550 nm) but must also have low electrical resistivity in order to provide high enough electrical current at the operating voltages to generate sufficient heat to the filter (spacer layer). Materials which can satisfy these requirements include but are not limited to polycrystalline, microcrystalline or nanocrystalline silicon, indium tin oxide and zinc oxide. To optimize heater operation, note that power density=$V^2d$/rho $L^2$. That is, power density goes as square of (V/L) but only linearly with thickness d.

As mentioned above, one method of driving the heater, based on the TTFF's thermal architecture involves supplying a current spike to the filter heater layer—which heats the filter very rapidly—and make measurements during the cooling process. In an analog circuit, the current spike could simply be the result of a capacitor discharge. With the proper thermal and electrical design, a relatively linear curve can be achieved.

According to a second method, the filter is set to a specific wavelength, stabilized at this wavelength, and then a measurement is taken. This allows for very high accuracy at a specific wavelength, assuming the wavelength can be locked well.

Several methods may be used to measure wavelength as the scan or wavelength setting occurs, regardless of the method by which the scan or wavelength setting is performed. Several are now described.

Pre-calibrated curves defining a steady temperature vs. time profile are used in one method to estimate wavelength being transmitted by the filter. If the TTFF is in a temperature stabilized environment, no additional measurement or computation is required, since it may be assumed that the temperature vs. time profile remains constant over the OCM's operational life. However, if the TTFF is not temperature stabilized, the temperature vs. time scan profile will likely change. The addition of a thermistor to measure TTFF assembly temperature and a series of calibrations at different ambient temperatures allows a reasonable estimate of wavelength vs. time to be obtained.

According to another method, the TTFF temperature can be directly measured using temperature-dependent thin film resistors (thermistors) that are integrated with the device. Since wavelength is directly related to temperature in the TTFF, such a measurement gives a very good instantaneous estimate of transmitted wavelength. In order to produce a result that correlates well with the filtered wavelength, measuring the temperature of the device should be done accurately and should be localized to the place where the light goes through the device, which is a small portion of the device area. Three possible configurations are now described.

The thin film heating element in the TTFF can be used as both the heater and the temperature monitor. To implement this, a small amount of current should be run continuously into the film and the voltage over the film measured. The relationship between current and voltage may be monitored to determine film resistance, and therefore, temperature. One potentially superior way of providing these measurements is to superimpose a small AC signal over the heating current, at a frequency sufficiently high relative to the TTFF's thermal time constant such that it essentially results in very small DC heating, and measure resistance directly in this manner. A simple analog circuit could be constructed to provide this function and not interfere with TTFF operation. It would provide a single analog output that is a function of the heater's resistance, representing temperature, that would in turn be used to determine filter wavelength.

Because, in some configurations, the temperature of the heater film may not accurately represent the overall temperature of the filter, particularly if it is on one side of the TTFF, it may be preferable to insert another thermistor layer into the structure which better reflects active layer temperature. Such a layer may be made of very similar materials to the heater, for example, ZnO, polycrystalline silicon, bulk crystalline silicon, thin metal lines, and many others, and may be measured in much the same manner as described above, including the AC signal. It should be noted that the ideal layer for both temperature measurement and heating is the cavity layer in the TTFF. Even if the materials constraints do not allow for direct heating of the spacer layer, it would be highly advantageous to use this layer as a thermistor, which can be done even with highly resistive materials, given the correct circuit, in order to get very accurate wavelength determination.

For even more accurate temperature measurement, both the heater layer and another layer in the film, preferably placed on the opposite side of the spacer from the heating layer, should be used. The combined measurements of these films together with a simple model for thermal flux will give very accurate numbers for spacer film temperature and therefore transmitted wavelength.

The most accurate method of determining wavelength is to measure it optically using calibration methods. At least three possible methods are now described.

The fiber optic network system which is the target of the OCM can be configured to contain calibrated optic signals at reference wavelengths which may be monitored by the OCM. Preferably, there are at least two such reference wavelengths so as to provide "end markers" on each bound of the band. However, this approach has not presently been adopted in commercial communications equipment and so it cannot be relied upon.

A stable wavelength reference source can be built into the OSA or OCM. Many OCMs and optical spectrum analyzers indeed take this approach. An LED, which has a relatively broadband emission, together with a filter, for example a stabilized Fabry-Perot etalon, are used to create a wavelength reference. The advantage is a stable, absolute reference. The disadvantages include more expensive components and packaging, additional reliability concerns, and expanded packaging size.

Figure 38:
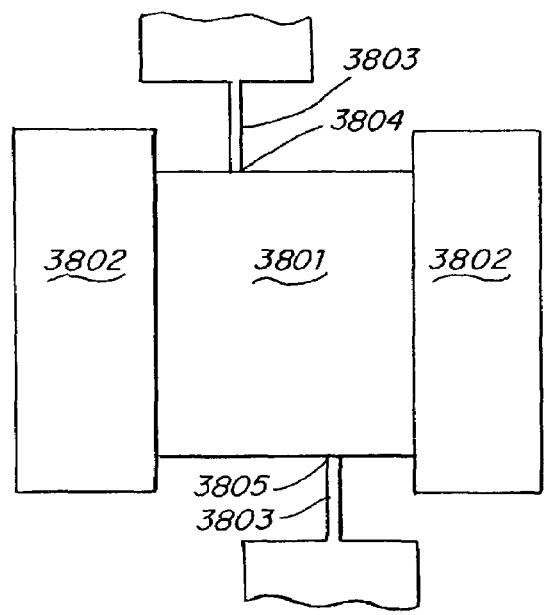
FIG. 38 is a top view of a filter heater with a four-point contact arrangement.

Because heat is dissipated through the thermally conductive contact pads and substrate, the temperature across the entire heater using either of the first two approaches is not uniform. Thus the temperature measured by one of these two-point methods does not accurately correspond to the temperature at the spatial position at which light is transmitted. A solution, as shown in FIG. 38, is to use four, instead of two, electrical contacts, i.e. a four-point probe to measure only the center resistance during heating. Heater 3801 is supplied with heater current through contacts 3802. Two tiny probes 3803 extend to points 3804, 3805 on opposite edges of the heater film 3801, near the center, so as to measure only the center resistance during operation. The conductor forming these traces 3803 has to be thin so that it does not itself affect temperature uniformity.

According to a third approach, an additional optical element in the light path can be used to create regular, fixed disturbances in the transmission spectrum. For example, a Fabry-Perot cavity with relatively weak mirrors and a cavity large compared to the wavelength will have this effect of creating a "ripple" on top of the incoming transmitted light. Because it is a fixed pattern with a known effect, this ripple may be easily separated out of the overall signal received during wavelength scan. The signal may then be used as a "scale" for the true signal data that was gathered during the scan, both on a relative and absolute scale. Such a cavity and function may be easily integrated into the TTFF. The substrate on which the filter is constructed may in fact serve as a Fabry-Perot cavity for this purpose. It will be temperature stabilized, at least for high-resolution applications where such a scale is really necessary. On the electronic side, this "pilot tone" could be picked up by an analog circuit to measure the "rate of ascent/descent" in wavelength during a scan. Note that this method of wavelength referencing may be applied not only to the TTFF, but to other types of tunable filters as well.

In short, there are many ways to estimate wavelength for each detector data point collected, ranging from a one-time calibration in the factory to continuous optical signal monitoring. Several of these methods lend themselves to low-cost implementation in the TTFF-based OCM package.

We now turn our attention to a more detailed discussion of materials As previously mentioned, materials suitable for the embodiments described herein should possess a combination of excellent transparency at the wavelengths of use, large thermo-optic coefficients, low scattering, high adhesion both between layers and between the stack and the substrate, compatible coefficients of thermal expansion and stable properties over repeated temperature cycling by several hundred degrees Celsius over a long service life. Also, the materials should be formed and deposited with accurate, uniform thickness and properties. Plasma enhanced chemical vapor deposition (PECVD) is useful for depositing layers of hydrogenated amorphous silicon (a-Si:H) and related materials as thin film filters. While any material suitable for making a Fabry-Perot filter or other structure, and having a useful thermo-optic coefficient could be used, we now describe the a-Si H and related materials as suitable examples.

It is desirable to control the index of refraction of the various films, in addition to their physical, and thus optical, thicknesses. PECVD is a well-established technique for deposition of thin films of semiconductors and dielectrics such as $SiO_2$, a-Si:H, and a-$SiN_x$. Many filters, including the Fabry-Perot thin film filters discussed above include alternating layers of high and low index material. Others use a continuously varying index to make a rugate filter (see Applied Optics 25 (16), p. 2644 (1986) by P. Baumeister). Making other of these structures requires having control over the index and thickness of the various materials used.

The low refractive index of a-SiN, and the relatively high index of a-Si:H, 1.77–2.05 depending on gas mixtures and 3.62 at 1.55 μm, respectively, in our process, can be used to make mirrors with reflection bands centered on 1550 nm. All layers of the mirror portions of the film stack are one quarter wave optical path length, that is nd=λ/4. In the spacer layer, we use a-Si:H, with its high thermo-optic coefficient with an optical thickness of a half-wave or a multiple thereof resulting in a thermally tunable filter. Thus, only two compatible materials are used. By varying the refractive indices of these materials, for instance slowly changing the composition of the a-SiN$_x$ to a-Si:H (in the PECVD process, decreasing the ratio of the flow of NH$_3$ to SiH$_4$) we can alter the index from 1.77 to 3.62 in a quasi-continuous fashion. Furthermore, by adding GeH$_4$ to the gas mixture in the plasma, we may increase the index of the spacer layer and of the high index layers of the mirror stacks to 4.2. Increasing beyond this point does not improve the filter performance further because the a-SiGe:H starts to absorb more strongly beyond a certain fraction of Ge. Thus, by varying the plasma chemistry and deposition parameters, we are able to control very well the refractive index and the thickness of these thin films.

Materials for the heater layer are now discussed. The heater material should be a material which is compatible with the other materials mentioned including the thermal budget and chemical processing associated with their production, and which can be used as a heater. Presently preferred is to use a conductive thin film of the proper index which serves simultaneously as an optical layer of the filter and also as the resistive heater. Therefore the material should not scatter or absorb the light, should have a proper index of refraction, and must have a conductivity large enough that running current through it will not require a very large voltage. Several potential candidates exist, the leader of which is polycrystalline silicon. Others include transparent conducting oxides, degenerately doped wide-gap semiconductors and doped micro- or nano-crystalline silicon.

Transparent conducting oxides (TCOs) include compounds such as indium tin oxide (ITO) SnO$_2$, and ZnO. The latter two are doped with either aluminum or fluorine to achieve a useful conductivity. However, this doping also increases their free carrier absorption which may render them too absorbing in some applications. These films are deposited by sputtering a target in an inert (e.g., Ar) atmosphere or in a reactive atmosphere (e.g. O$_2$). TCOs have a useful conductivity (200 S/cm–1000 S/cm has been seen. By depositing thin films (~100–200 nm) potential absorption problems are minimized. Furthermore, these films are generally resistant to damage from the temperatures and plasma processes used to deposit the a-Si:H based films.

The terms polycrystalline, microcrystalline and nanocrystalline silicon are used somewhat interchangeably in the semiconductor industry to describe films with various scales of structure. In any case, they can be doped with either phosphorous or boron and also be used as the resistive element. N-type μc-Si can be produced with conductivities of 10–20 S/cm. Furthermore, up to 39 S/cm can be obtained for boron-doped, p-type, μc-Si films. Micro-crystalline Si is also compatible with a-Si:H deposition using the same capital equipment with slight modifications to the deposition recipes. Furthermore its absorption at 1550 nm is minimal, similar to crystalline or amorphous silicon. During growth of Mc-Si, its surface can become relatively rough. It may have an AFM mean surface roughness of ~33 Å compared to ~3 Å for a-Si:H, which causes scattering of the light. However, by chemically and mechanically polishing the surface after deposition of μc-Si this surface roughness can be made smooth allowing for direct incorporation of μc-Si into the filter as the heating element. Re-crystallized doped polysilicon has a smooth surface and the appropriate conducting and optical properties to form the heater layer.

Figure 10:
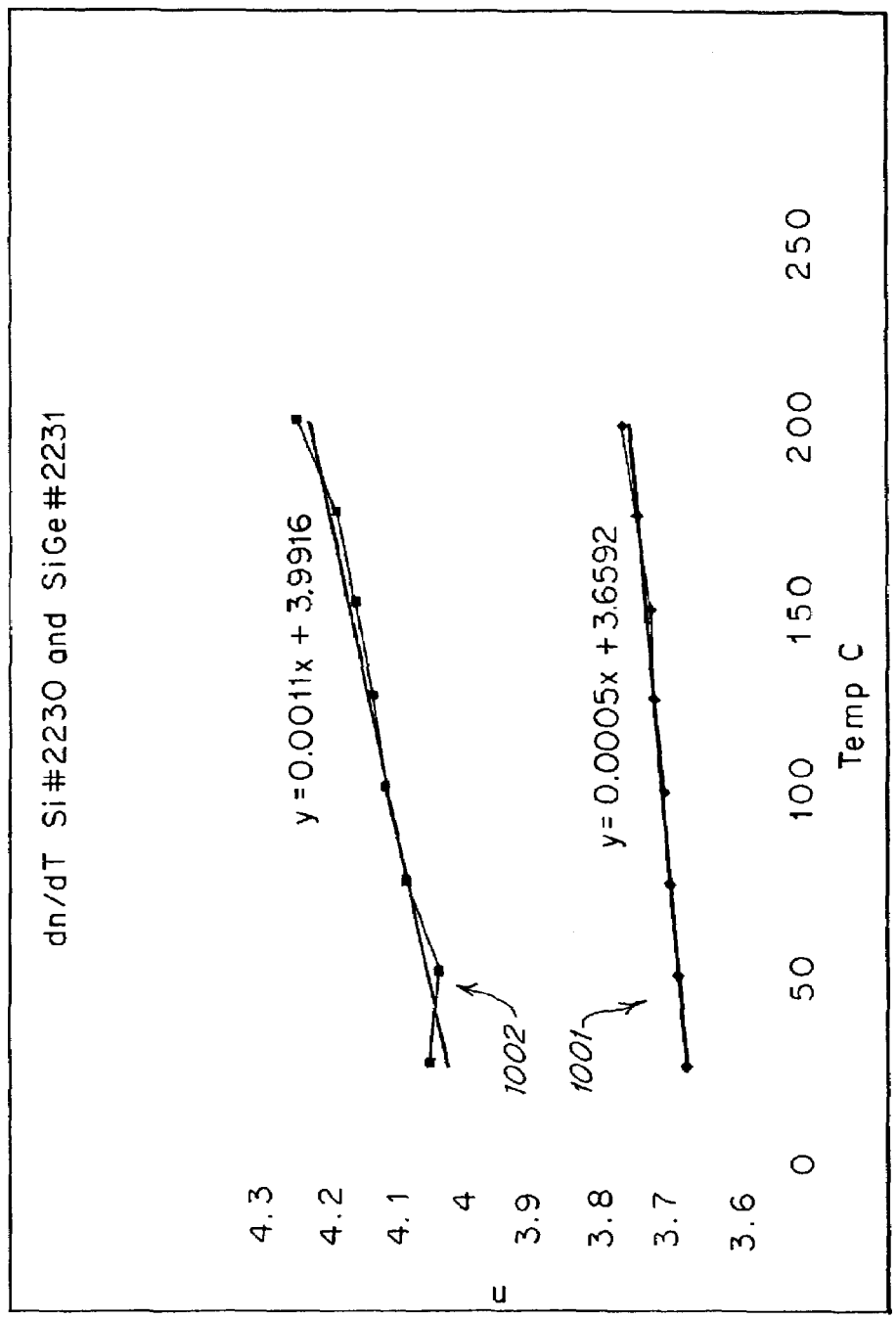
FIG. 10 is a graph of dn/dT comparing a SiGe alloy having superior thermo-optic characteristics to Si.

The physics of the thermo-optic coefficient, i.e., the change of index with temperature, dn/dT of thin film direct-deposited semiconductors are only partially understood. However, while taking into account other considerations given herein, the highest coefficient film possible should be used. The best published values indicate dn/dT=5×10$^{-4}$/K for c-Ge at 1.9 μm (J. Phys. and Chem. Ref. Data vol. 9, p. 561 (1980) by H. H. Li) and 1.9×10$^{-4}$/K for either crystalline or amorphous Si. FIG. 10 shows the measured dn/dT over a temperature range 25–200° C. We have prepared a-Si:H samples with dn/dT=3.6×10$^{-4}$/K, shown in curve 1001, thought to be larger than any published value. Also, we have demonstrated, as shown in curve 1002, dn/dT=11×10$^{-4}$/K for an alloy sample prepared by us with 22% Ge and 78% Si in the gaseous phase. This is a value which exceeds any known by us to be reported in the scientific literature for thermo-optic semiconductors.

Figure 11:
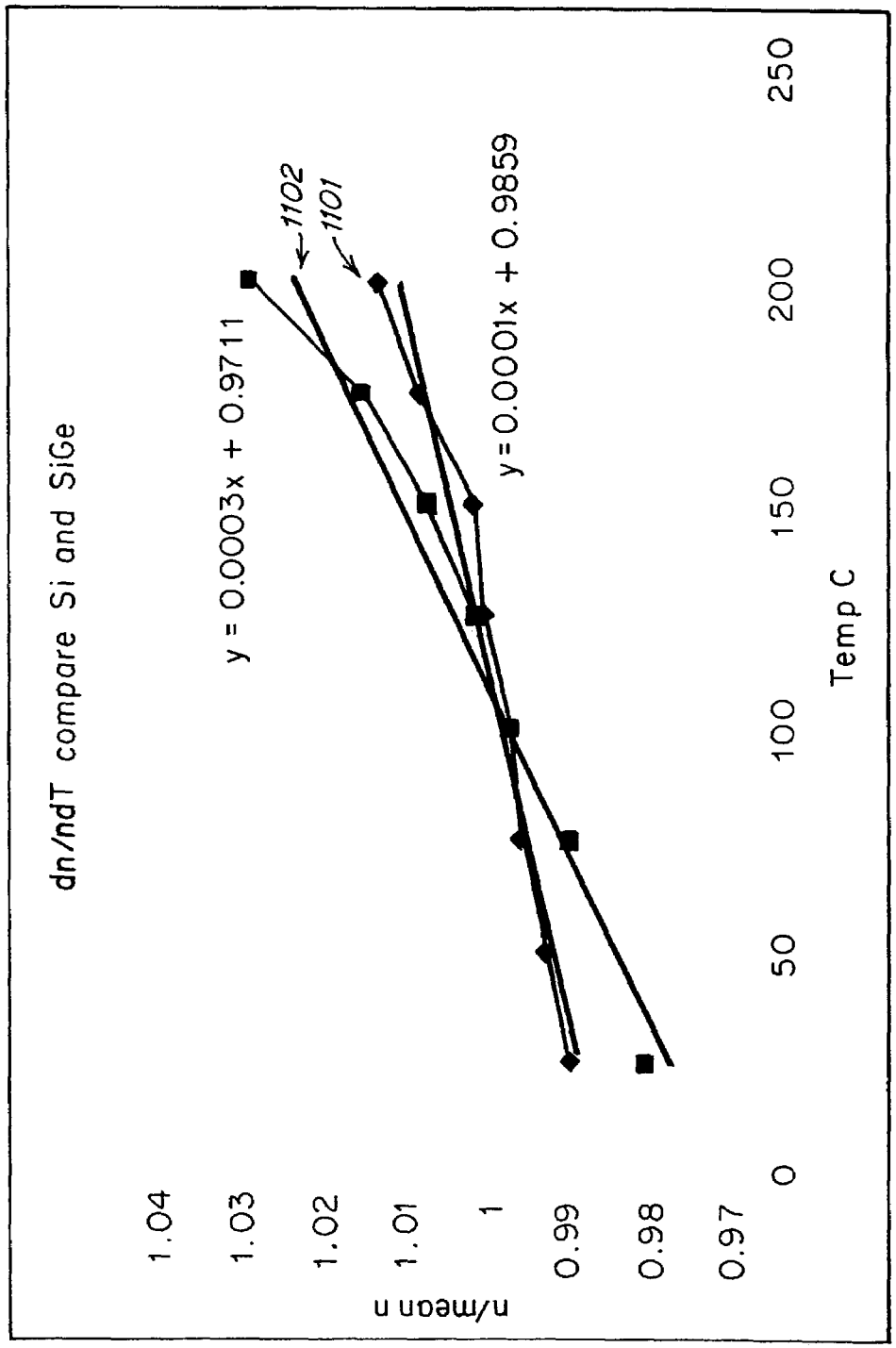
FIG. 11 is a graph of dn/ndT comparing the SiGe alloy and Si materials whose properties are shown in FIG. 10.

FIG. 11 shows the measurements of FIG. 10 plotted as 1/n dn/dT, as is relevant for the fractional change of optical path length in the spacer layer of a TTFF.

For the Si, dn/ndT=1×10$^{-4}$/K as shown in curve 1101.

For the SiGe sample #2231, dn/ndT=3×10$^{-4}$/K as shown in curve 1102.

Using the a-Si option, we predict, using any mutable method of computing the center wavelength of a filter structure a tuning range exceeding 40 nm in a thin film stack as described. This range has been verified by experimental observation. In summary, using a-Si:H we have constructed free space filters without moving parts having tuning ranges in excess of 40 nm.

Now that the foundational design principles and materials have been established, a particular embodiment is described. In this embodiment, the heating takes place through a layer of polysilicon deposited over the substrate and under the filter film stack. This is preferable for some applications to placing it adjacent to the spacer in the interior of the stack, because the materials for this example are somewhat absorptive in the near IR and will therefore degrade filter transmission if used in regions where the light makes many internal reflections. However, only one pass is made near the substrate.

This embodiment is made using a PECVD process as described above for deposition of the optical films. Other methods, such as e-beam evaporation or ion-assisted sputtering can also be used. However, processes that give higher energies to the deposited atoms result in denser, more stable coatings; in PECVD, this means use of high frequency, high power discharges. PECVD is able to produce even coatings on non-flat surfaces, and the thickness control of PECVD is conveniently accomplished by gas valves, in some cases pulsed valves for "digitized" deposition. This method is sufficiently repeatable that in situ optical monitoring may not be needed, an advantage over PVD.

As an illustrative example, consider the thin film formula for a Fabry-Perot resonator is deposited on a substrate, such as glass, fused silica, sapphire or Si wafer, as follows:

$$\text{Substrate}|Z(HL)^4S(LH)^4Z|\text{air}$$

Z=quarter wave of n-doped polysilicon;
L=quarter wave of low index material, such as SiN, n=1.77, or, alternatively, SiO$_2$, n=1.44;

H=quarter wave of high index material, such as a-Si:H, n=3.4; and

S=integral number of half waves of high index material.

In this exemplary embodiment, S can either be two half waves of pure a-Si:H or, alternatively, for enhanced thermal tuning, two half waves of a-SiGe:H (21.66% Ge in the gas phase), n=4.2 at 1.5 μm.

All optical path lengths are computed relative to 1550 nm. Thus, a quarter wave layer has a physical thickness determined by:

$$n \times d = 1 = \frac{1}{4} 1550 \text{ nm};$$

where:
n=index of refraction;
d=physical thickness; and
l=optical path length.

Because of the low index of $SiO_2$ (1.44 at 1500 nm), the structure will have improved mirror reflectivities with the same number of HL cycles, leading to narrow passbands. A quarter wave optical thickness of each material would then be as follows:
260 nm of $SiO_2$
114 nm of a-Si:H
219 nm of SiN
92 nm of a-SiGe:H These thicknesses can be determined by depositing test films on glass substrates and observing their reflected spectra; a quarter wave will have max reflectivity at 1500 nm and zero reflectivity at 775 nm. Using the same valve-controlled deposition times in the Low-High stacks then results in accurate quarter wave stacks; a more accurate method is the use of pulsed gas valves, which "digitize" the depositions. In "digitized" deposition, known numbers of very short pulses of gas produce known thicknesses. In situ optical monitoring can also be used for more accurate layer thicknesses by observing the "turning points" in transmission or reflection, indicating the proper termination of each layer.

Inaccuracies in deposition thicknesses and other physical parameters affect final performance. Some simple computations will help to illustrate the effect of various perturbations in thermo-optic filter fabrication.

All the above films have been previously described. FIGS. 12–17 show the effect of various variations.

Figure 12:
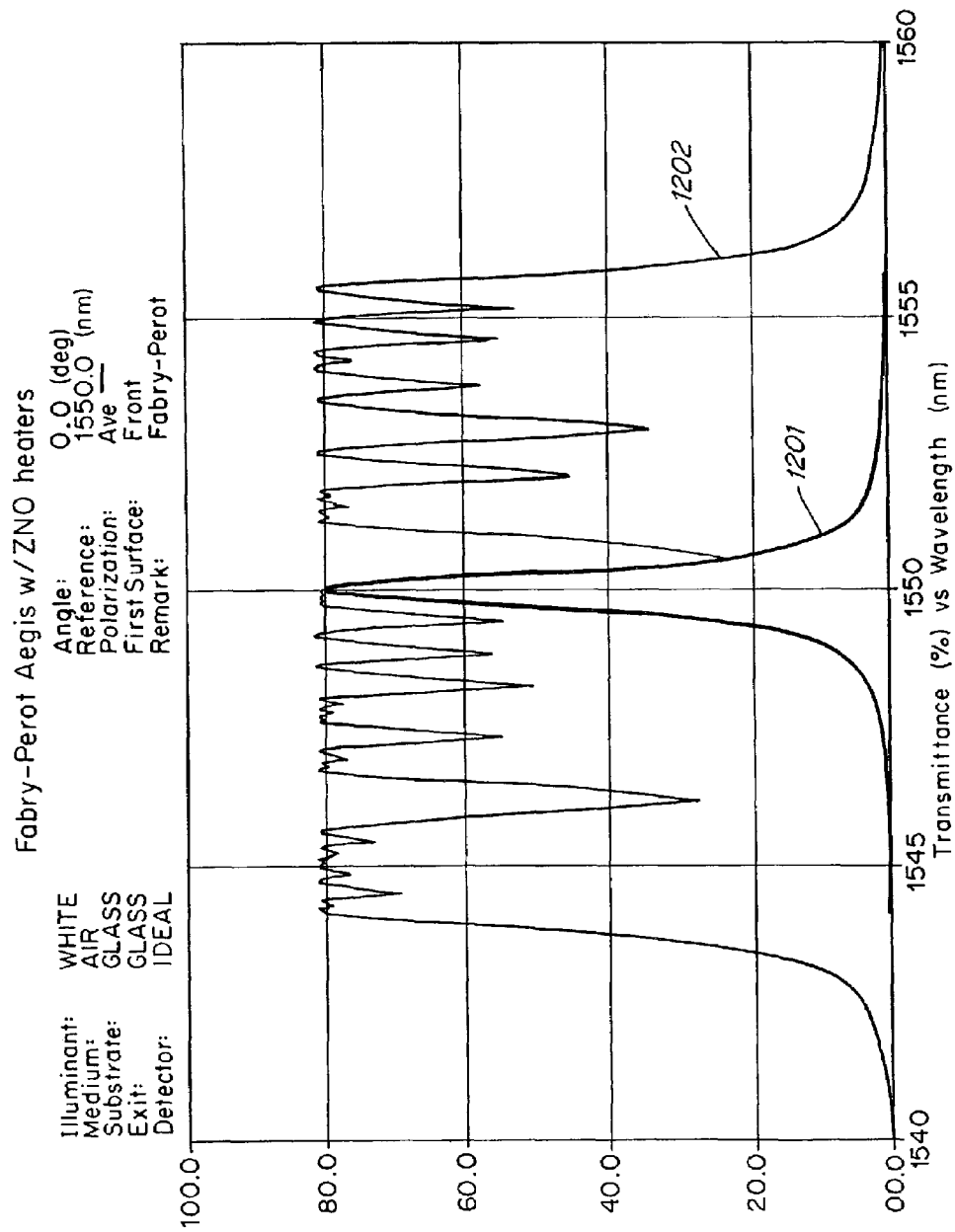
FIG. 12 is a graph of transmittance v. wavelength comparing a Fabry-Perot filter nominal design to the filter with up to 0.5% thickness errors in the deposition of the layers.

FIG. 12 shows the effect of randomly varying the thickness of the films by small errors of 0.5%, a very close tolerance for thin film deposition. Note that the effect is to shift the nominal filter characteristic 1201 side to side within an envelope 1202, but not to distort the filter shape or affect insertion loss significantly.

Figure 13:
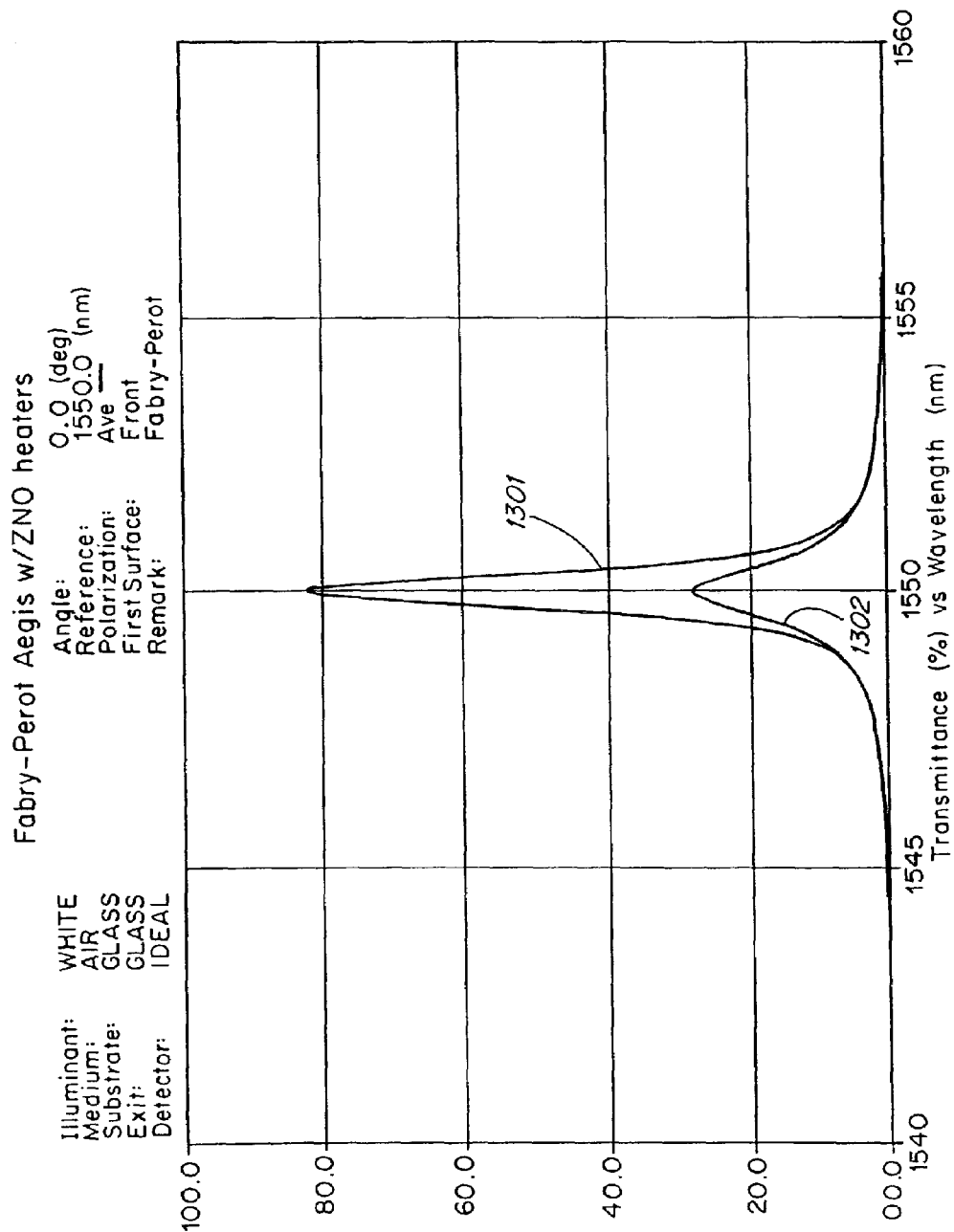
FIG. 13 is a graph of transmittance v. wavelength comparing a Fabry-Perot filter nominal design with no absorption in the spacer to the filter with an absorption coefficient, k=0.001.

FIG. 13 shows the effect of introducing a small amount of absorption (or equivalently, scattering) into the spacer only. Spacer with k=0 has 80% transmission as shown in curve 1301; if k=0.001 at 1550, the transmission is down to 28% as shown in curve 1302. This illustrates the importance of low absorption, low scattering, high optical quality transparent materials. Preferably, $k<1 \times 10^{-5}$.

Figure 14:
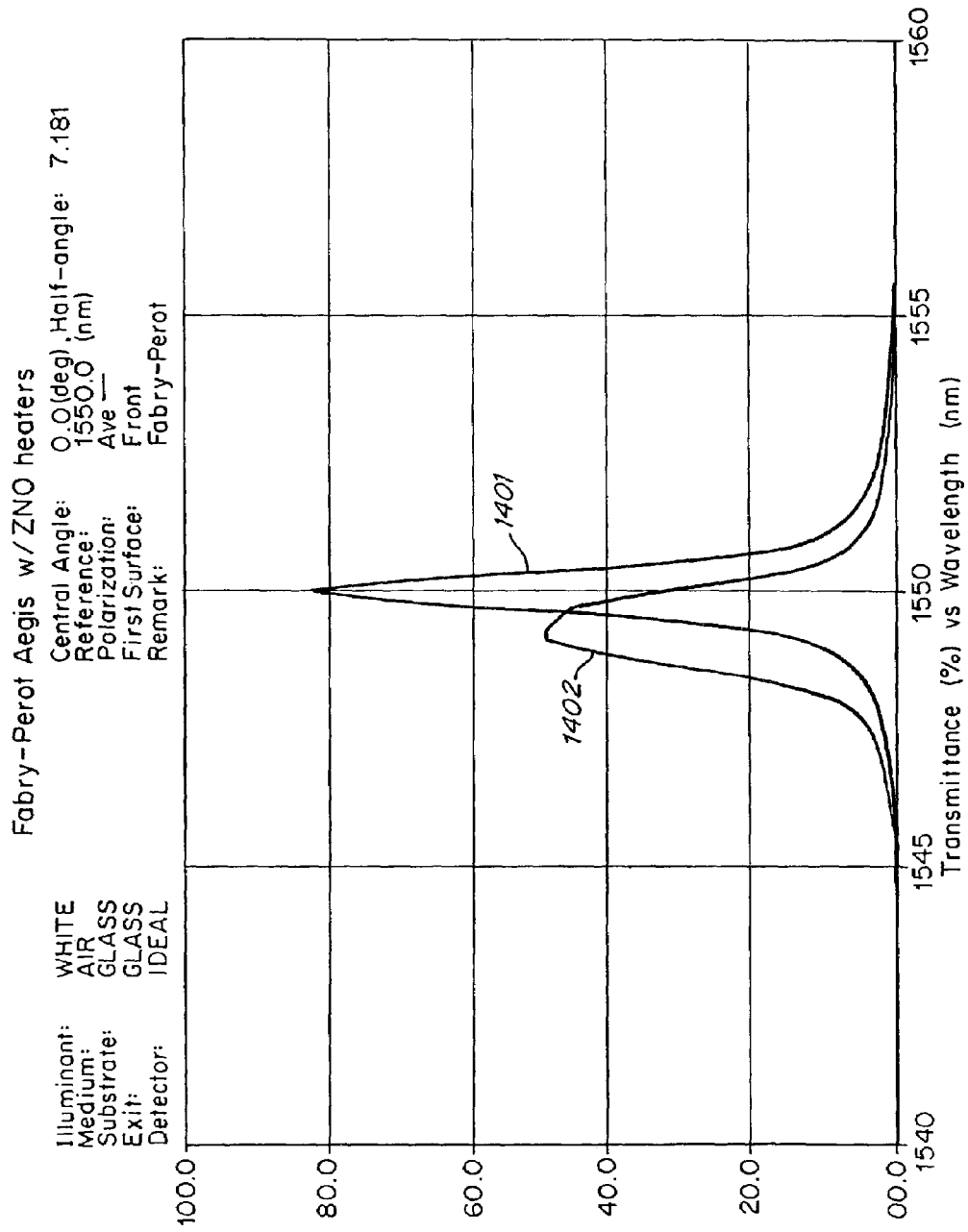
FIG. 14 is a graph of transmittance v. wavelength comparing a Fabry-Perot filter receiving a collimated light beam to the filter receiving light from a single mode fiber without collimation.

FIG. 14 shows the effect of noncollimated light input. The filter characteristic with collimated light 1401 is compared to light from a single mode fiber (no lens) with a numerical aperture of 0.12 corresponding to a 7° half angle light cone 1402. When packaging is discussed, below, the option of including a collimating lens is noted.

Figure 15:
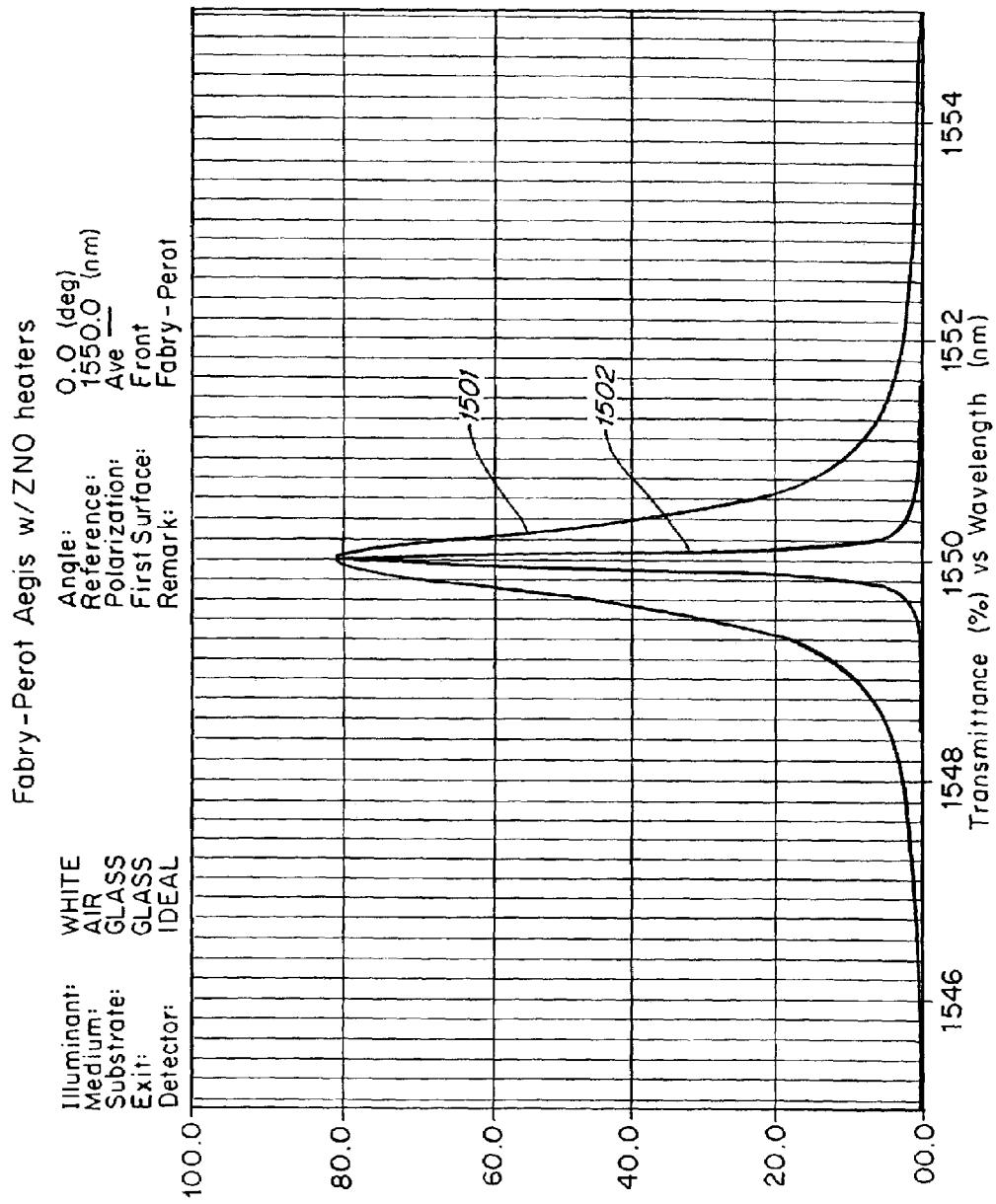
FIG. 15 is a graph of transmittance v. wavelength comparing a Fabry-Perot filter nominal design to the filter with a higher contrast ratio between refraction indices of the mirror layers.

FIG. 15 shows the advantage to be obtained by increasing the index contrast between H and L layers of the mirror stack while keeping the number of HL cycles (4) unchanged. In this example, the use of SiN for L is compared in curve 1501 with $SiO_2$ for L in curve 1502, with H remaining unchanged (a-Si). The effect is to dramatically narrow the pass band.

Figure 16:
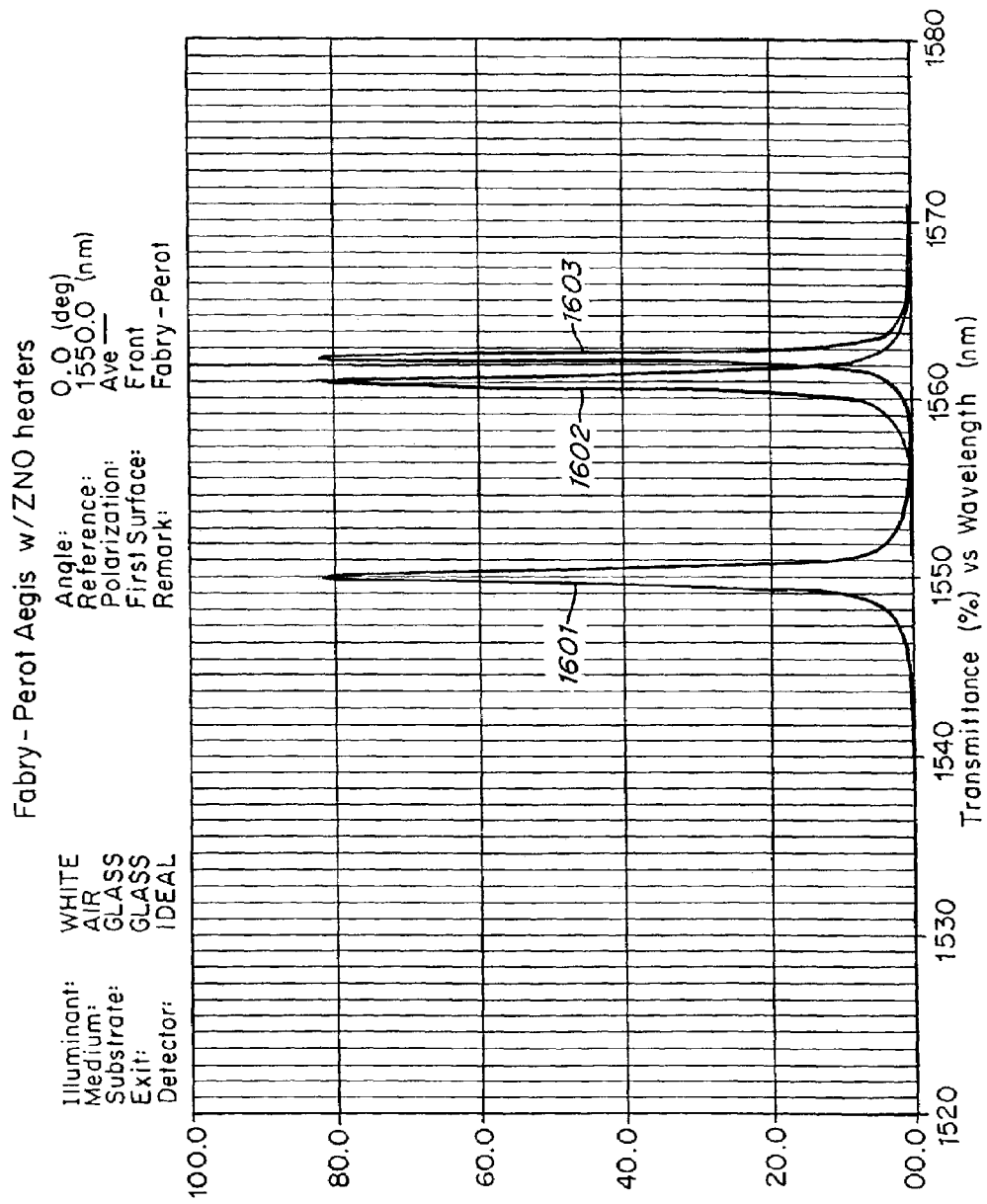
FIG. 16 is a graph of transmittance v. wavelength comparing the tuning range of a Fabry-Perot filter nominal design to the filter with a thicker spacer layer.

FIG. 16 shows the advantage to be obtained from a thicker spacer with respect to thermo-optic tuning range. The baseline passband of curve 1601 is with dn/n=0, i.e., no tuning applied. The next curve 1602 is for dn/n=0.01 in the case the spacer is two half waves in thickness. The rightmost curve 1603 is again dn/n=0.01 but with a spacer of three half waves. The tuning range is modestly improved, about 10%.

Figure 17:
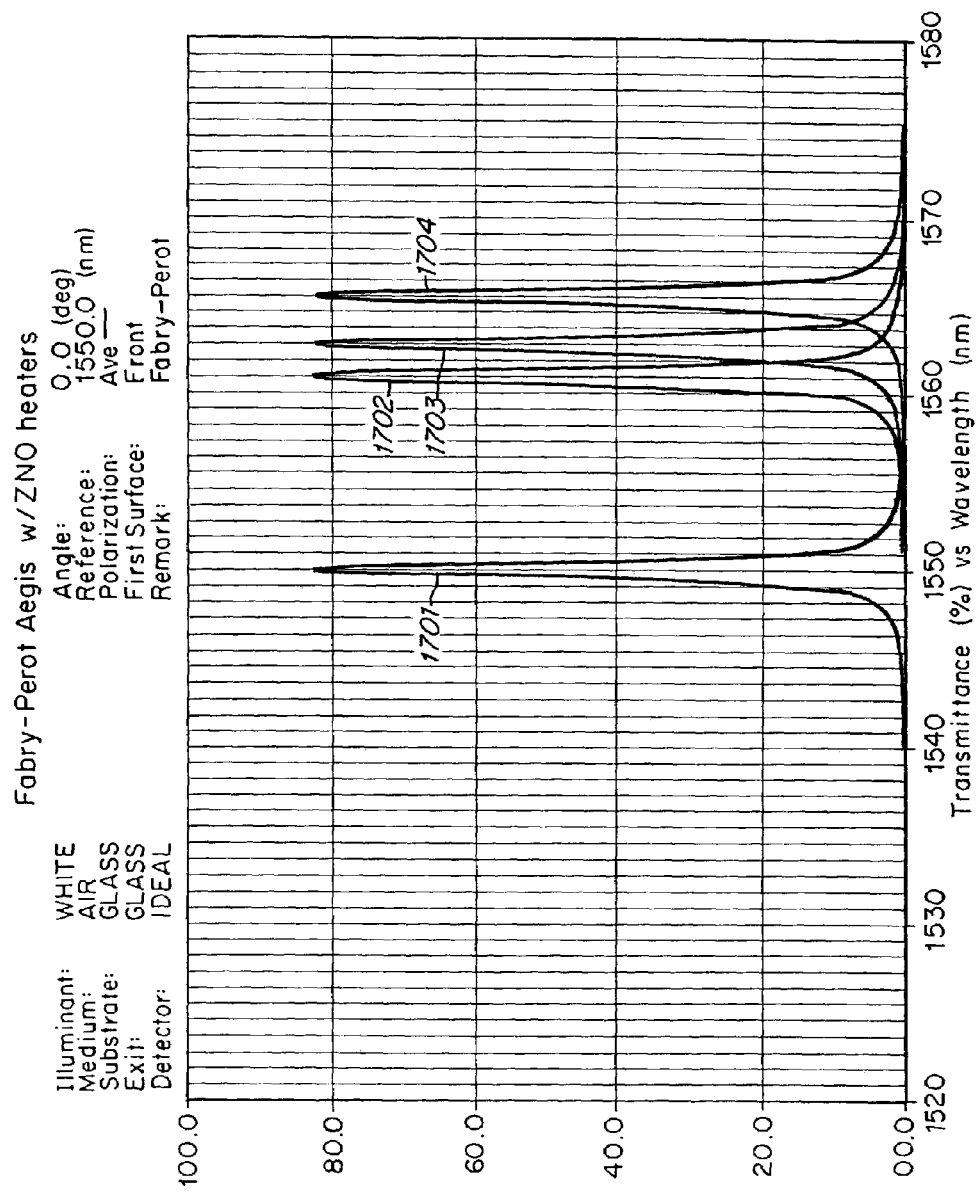
FIG. 17 is a graph of transmittance v. wavelength comparing the tuning range of a Fabry-Perot filter with only the spacer having thermo-optic properties to the filter with the spacer and the high index mirror layers having thermo-optic properties and to the filter with all layers having thermo-optic properties.

FIG. 17 shows the effect if not only the spacer but also the H and L layers of the mirror stack are thermo-optically altered at the same time. The baseline curve 1701 at 1550 is with no temperature change. The curve 1702 is with only the spacer thermo-optic. The curve 1703 has the spacer and also the H layers thermo-optic, similar to our case. The curve 1704 shows all films, including spacer, H, and L with the same thermo-optic coefficient. Thus the tuning range of the filter is significantly improved if several mirror high index layers are thermo-optically tunable, not only the spacer. Thus thermal tuning is enhanced by heating all of the layers, not just the spacer, and by making the mirror stacks, or at least the H layers, out of thermo-optic media similar to the spacer. For example, if only the spacer is thermally tunable, then d(wavelength)/wavelength≈⅓ dn/ndT, but if all the films are equally thermally tuned, the factor ⅓ becomes closer to 1.0.

It is instructive to recognize that in the past, semiconductors and other thin film materials with large thermo-optic coefficients have has been avoided by the thin film WDM filter industry specifically to avoid temperature sensitivity. In the technology described here, we have turned this upside down by maximizing this very property. Thus whereas conventional filters have shift of the center wavelength of a filter <0.5 picometers/degree, we have achieved tunability>150 picometers/degree. Thus we have discovered that a property thought to be detrimental to high-quality optical devices, namely the temperature sensitivity of semiconductor films, could be used to produce, to the best of our knowledge, the most highly tunable thin film filter ever constructed.

In the foregoing, the detector component of the OCM has been assumed to be a conventional discrete detector, such as InGaAs. However, it is also possible to incorporate thin film PIN detectors made of doped versions of the very same materials already utilized for their thermo-optic properties. We now describe a further concept in which certain thin film layers internal to the filter serve as detectors.

Figure 18:
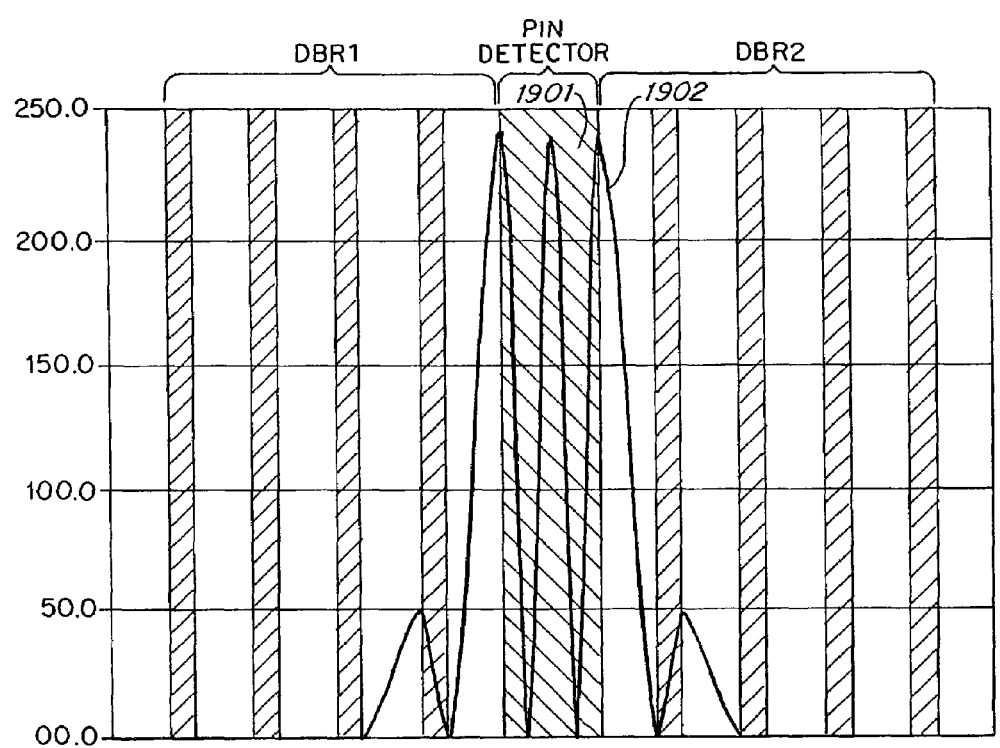
FIG. 18 is a graph of field intensity overlaid on a cross section view of a combined TTFF and resonant cavity enhanced detector.

In order to produce a complete measurement device, the TTFF can be combined with a detector, as follows. The TTFF includes one or cavities (FIG. 18, 1901) which create the effective passband. These resonant cavities see standing wave fields (FIG. 18, curve 1902) that are much in excess of the incoming radiation. As a result, if even a low-sensitivity, semi-transparent, detector (FIG. 18, 1901) could be placed in this cavity, it would provide a significant photoresponse, specifically at the wavelength to which the cavity has been tuned. This would allow a tunable filter that has a built-in feedback and monitoring mechanism, for example, an extremely compact spectrometer, in a single package where the tuning element and sensing element are contained in the same thin film stack, possibly even on top of a CMOS chip that acts as the driver for the system.

Semitransparent sensors can be included within thin film optical stacks operating at 850 nm, 1310 nm, or 1550 nm. These PIN detectors have very low absorption at 1550 nm (<<1%) and may be co-deposited with the films required for tunable thin film filters. Moreover, the materials used for the thin film PIN detector may be used for a thermally-tunable cavity in the TTFF. The principles of constructing such PIN detectors are set forth in U.S. patent application Ser. No. 09/813,454, filed Mar. 20, 2001, incorporated herein by reference. Transparent conductors are used to complete the PIN structure. These are composed of conductive materials that also do not have large loss at 1550 nm. Although in previous sensor structures we utilized ZnO or ITO contacts, the preferred contact material for resonant-cavity thin film sensors is doped micro-crystalline silicon. This material should be processed under conditions which ensure maximum conductivity in a very thin layer. Thinner layers are preferable both because of their bulk optical properties, since conductive material generally has a higher extinction coefficient, and because of the crystalline structure of these thin films, which increases dramatically with film thickness. Large crystalline structures on the surface of these films may cause scattering which may hinder the effect of the resonant cavity. However, methods for processing micro-crystalline films with high conductivity, small thickness, and very small crystalline structures have been demonstrated. One method is "closed-chamber" PECVD where the film is grown very slowly in a sealed machine, effectively simultaneously depositing and preferentially etching amorphous material, and leading to a very rapid transition to crystallites in the layer.

We now discuss examples of packaging of an optical instrument, for example the OSA or OCM disclosed above. The OSA, OCM or other instrument is not limited to any particular package style or carrier. Packages discussed here assume an input signal from an optical fiber.

Figure 19:
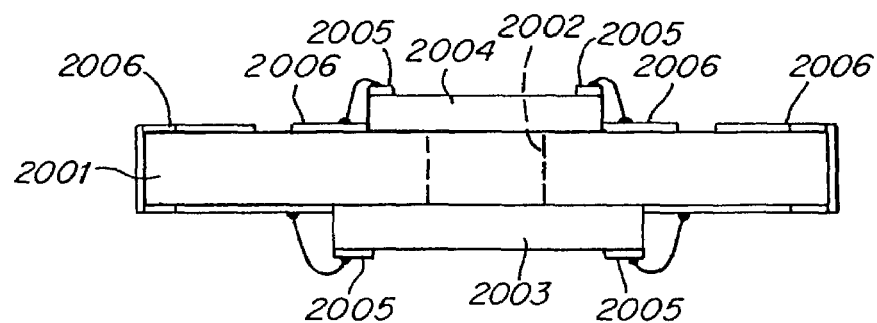
FIG. 19 is a side view of a chip carrier used to package a TTFF.
Figure 20:
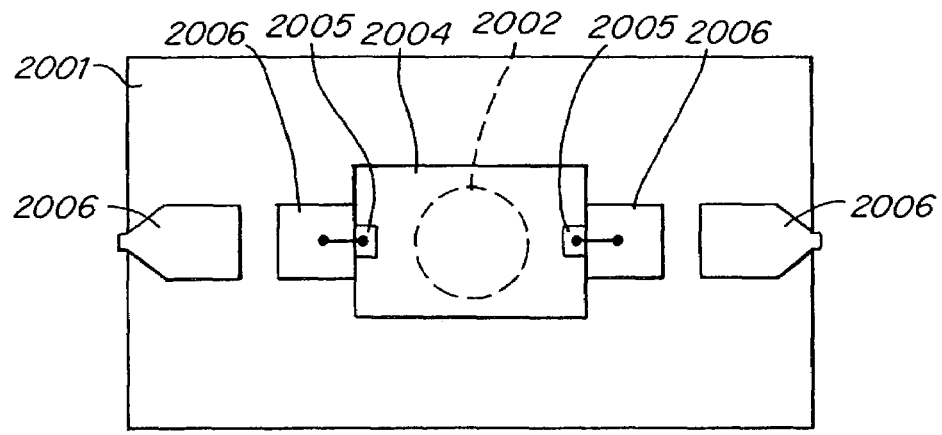
FIG. 20 is a top view of the chip carrier of FIG. 19.

There is a basic subassembly of a detector and TTFF, which is applicable across all of the packages described. Several configurations for this subassembly are illustrated in FIGS. 19 and 20, including a ceramic chip carrier 2001 with a through hole feature 2002. On one side of the carrier 2001 the detector 2003 is mounted, while on the other the filter 2004 is mounted, with electrical contacts 2005 made to the detector 2003 and filter 2004 and breaking out to external connections 2006 from there.

To optimize the package for both operational reliability and cost, it can be assembled in a standard transistor header chip carrier, for example a Transistor Outline (TO) can. TO cans are widely used for packaging both electronic and opto-electronic devices such as transistors, photodetectors, LEDs and solid state lasers. A large variety of TO cans are available which allows their flexible integration into a variety of applications.

A TO package includes two main components: the header (mounting surface) with integral pins hermetically sealed using a solder glass, and the cap. For optical components the cap incorporates a window, allowing external optics to propagate light into the sealed cavity. This allows construction of "terminal" devices such as Optical Channel Monitors (OCMs) and optical receivers or, conversely, source devices such as Vertical Cavity Surface Emitting Lasers (VCSELs) and tunable sources.

The TO headers described herein can be modified with an integrated feed through to allow the packaging of pass through optical devices. This feed through may be hermetically sealed in a number of ways, perhaps the most cost effective would be to use a window (or lens) sealed directly into the header surface, covering the feed through hole or tube.

TO headers are mass-produced in a stamping operation, often thousands at once. The manufacture of headers with integral feed-through tubes for use as electrical pressure sensors is also well known. This tube could be of any suitable diameter, restricted only by the inner diameter of the electrical pin circle, to accept optics such as ball lenses, optical fibers, gradient index (GRIN) lenses, etc.

The header would then be mounted with whatever optical component is to be packaged, aligned using any suitable method depending on the optics used, and electrical connections made as necessary. Procedures for welding caps to headers are widely known and therefore will not be discussed here. Any suitable method can be used. However, one alternative to the use of a standard window cap would be the use of a cap incorporating lenses as is commonly done for terminal devices. A feed-through, similar to that on the header, can also be integrated into the cap to house optics. See, for example, FIG. 36.

A package with three or more ports, such as that needed for Optical Add/Drop Multiplexers, can be constructed using widely available dual fiber collimators as the optical assembly mounted either on the cap, header or both. See, for example, FIG. 33. Custom free-space or GRIN optics could also be used to create multiple ports using a limited number of feedthroughs.

Figure 33:
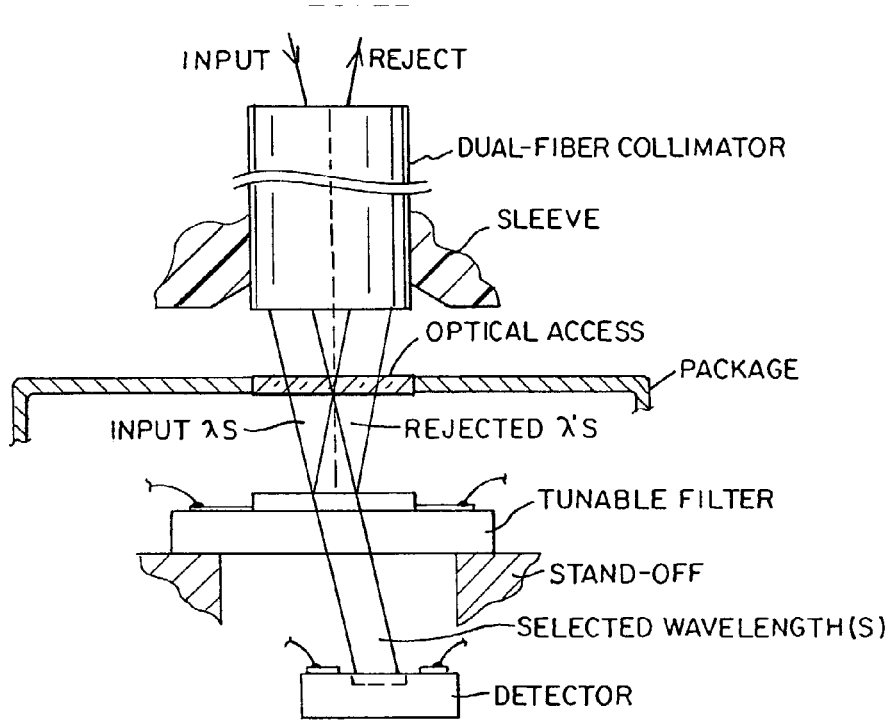
FIG. 33 is a cross section view of an optical assembly including an external dual fiber collimator used to introduce light-into the package and to receive light rejected by the filter in the assembly.

A generic configuration for a modular Optical Add/Drop Multiplexer using thin film tunable filters, such as disclosed in our application Ser. No. 60/310,047, filed Aug. 4, 2001 and incorporated herein by reference, can be packaged in a three port TO package as shown in FIG. 33.

TO style packaging technology was developed nearly 50 years ago for early transistors. Both TO headers and caps are massed produced to tight tolerances using proven stamping techniques resulting in header and window cap combinations often costing less than a dollar (windowless caps cost substantially less).

In addition to being low-cost, the most common TO packages, TO-46 are smaller than their more expensive counterparts such as the butterfly and miniDIL styles described above.

For ease of assembly, tolerances on the header, particularly the angular relationship between the mounting surface and the bore of the feed-through tube, should be tightly controlled. Loose tolerances can be avoided by careful quality control at the header/tube production and assembly level.

Figure 21:
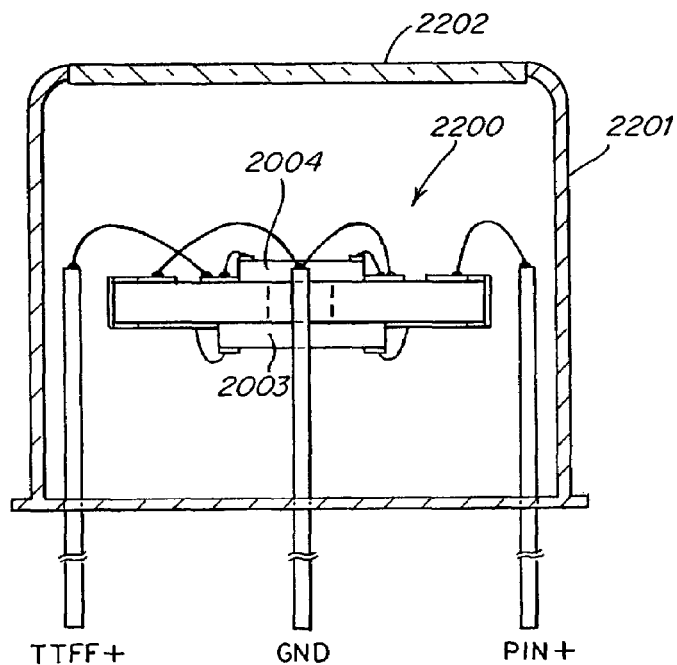
FIG. 21 is a cross section view of a transistor outline (TO) package into which the chip carrier of FIGS. 19 and 20 has been mounted.

FIG. 21 illustrates one simple package design including a filter and detector assembly 2200 hermetically sealed in a TO can 2201. In this design a 3-lead can 2201 with an optical access port 2202 is sufficient. The package can be pigtailed with an optical fiber, the port 2202 being either an anti-reflective coated lens to focus light onto the filter/detector assembly 2200 or a passive optical window to simply allow the signal to enter the can 2201. Using a relatively large area TTFF 2004 and detector 2003 simplify light coupling and optical alignment. External temperature control, signal conditioning and processing circuits may be used to enhance the capabilities of the monitor and need not be included in the package described. If a temperature sensor integrated into the TTFF is used, as described previously, the number of electrical contacts remains as shown in FIG. 21.

Figure 22:
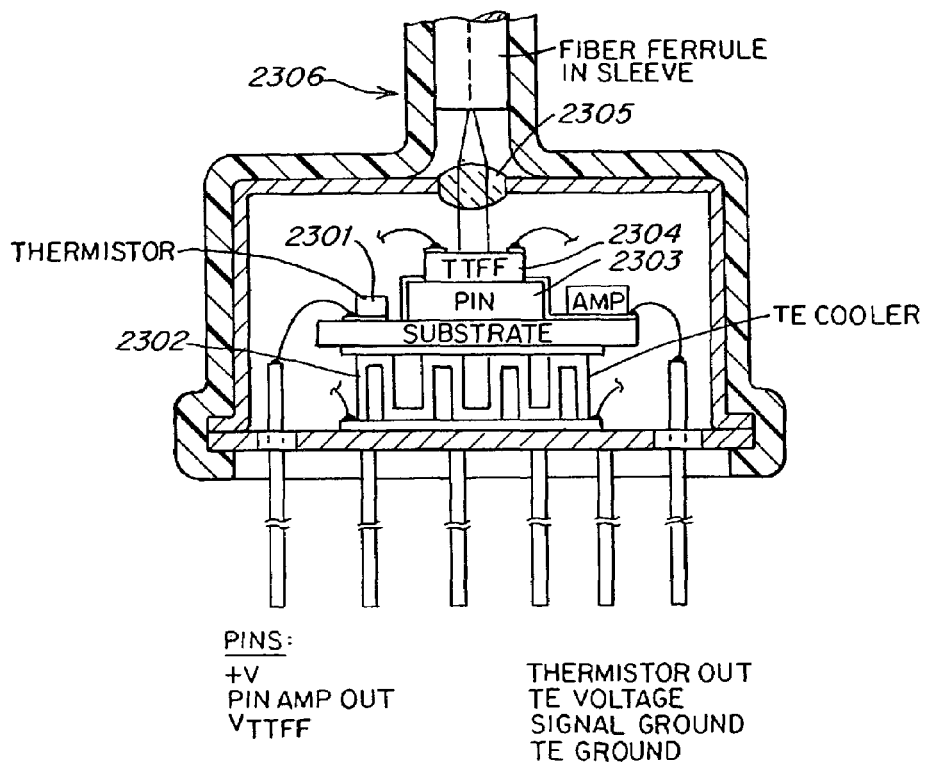
FIG. 22 is a cross section view of a TO package similar to that of FIG. 21, but into which a thermoelectric cooler has been also mounted.

A single discrete temperature sensor, for example a thermistor or semiconductor temperature sensor 2301, may be added to the package to monitor the temperature of either the substrate or the entire assembly, as shown in FIG. 22. The only change in packaging necessitated by a discrete monitor 2301 would be the addition of two more electrical contacts to the TO can for a total of 5.

To actively control the assembly temperature a small TE cooler 2302 may be introduced into the package as shown in FIG. 22. This active temperature control serves two purposes: it both lowers and stabilizes the operating temperature, which enhances sensitivity of the PIN diode detector 2303 and improves overall operation of both filter 2304 and detector 2303, contributing greatly to measurement accuracy and device longevity. This temperature control circuit also includes a temperature sensor for feedback.

The electronic circuits required to drive the temperature control unit/filter/detector and then condition and process the signal can be located external to the hermetically sealed volume, for example on a PC board. A larger TO can capable of accommodating the TE cooler and mounting on a heat sink is required. For optical connections the can may be pigtailed 2304 similar to FIG. 20, again using either a flat or lensed window 2305.

Figure 23:
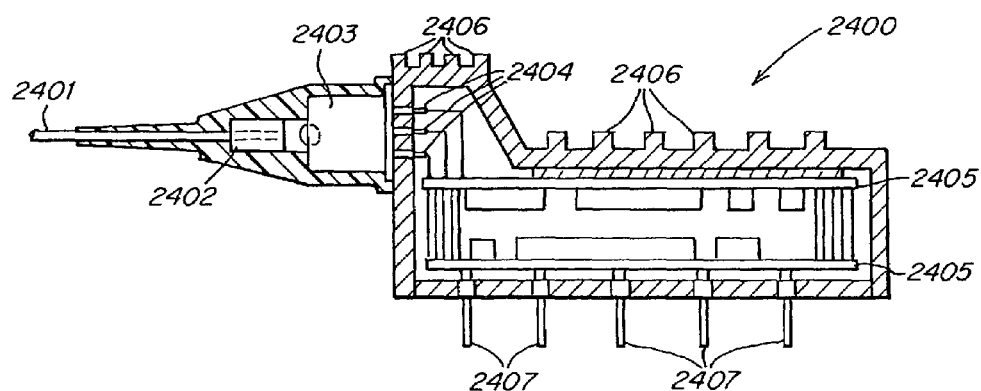
FIG. 23 is a cross section view of a complete optical instrument package.
Figure 24:
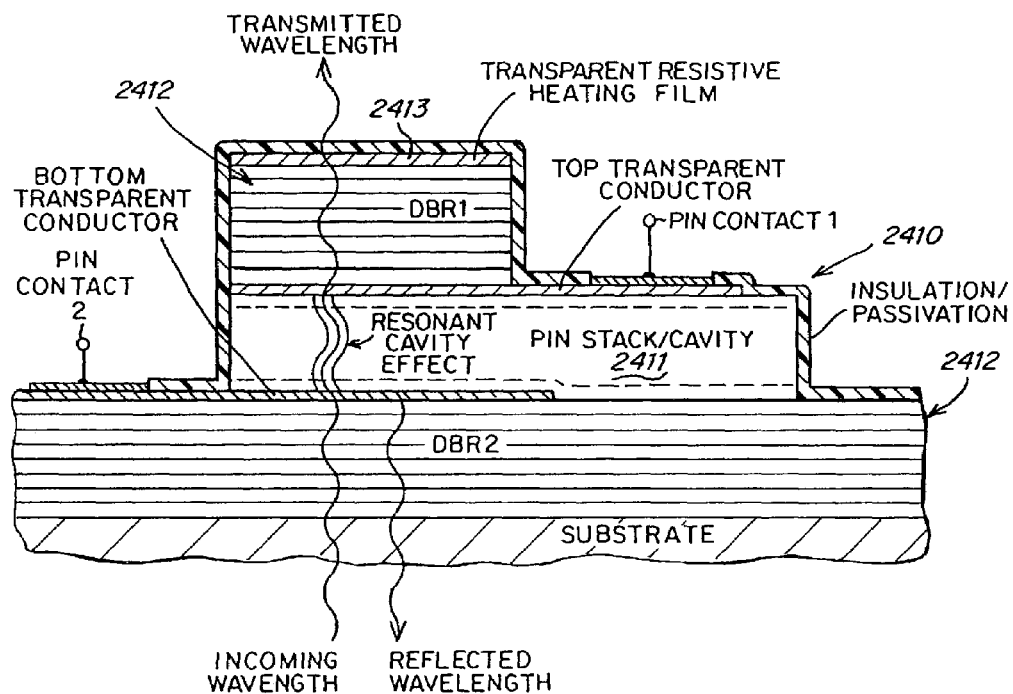
FIG. 24 is a cross section view of a thin film stack incorporating a resonantly enhanced PIN detector and a TTFF.

The most complete design of an optical instrument such as OSA or OCM would involve the integration of driving and signal processing circuits into one or several chips, all placed into a package 2400 which may or may not be hermetic, such as shown in FIG. 23, along with temperature monitoring and control devices. Though this configuration, particularly if hermetic, would be ideal from a reliability and accuracy standpoint, it drastically increases manufacturing costs for the entire device and is practical only in situations with strict performance and reliability requirements regardless of cost. As shown in FIG. 23, a fiber 2401 is adapted through a ferrule 2402 to provide an optical signal input to a TTFF, detector, etc. in a TO can 2403, as previously described. Pins 2404 of TO can 2403 carry signals between the elements within the TO can 2403 and external control and processing electronics on circuit boards 2405 in package 2400. Package 2400 can include heat sink features 2406 and pins 2407, connecting it to other circuits and systems.

Figure 25:
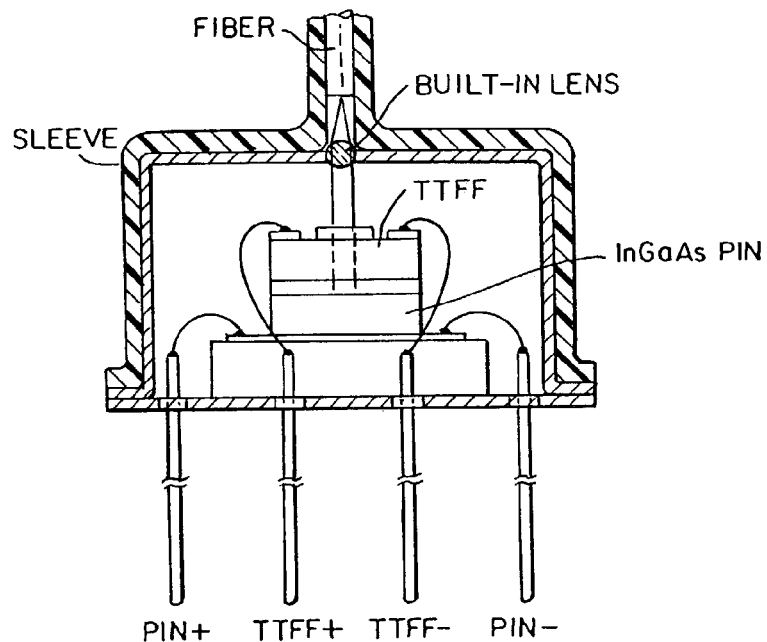
FIG. 25 is a cross section view of a TO package showing a fiber connection through the top.

FIG. 25 further details the structure of a thin film stack, including a cavity 2411, mirror stacks 2412 and a top heater 2413, which incorporates a resonantly enhanced thin film PIN detector instead of a discrete detector. FIG. 25 shows another perspective on the structure of an optical instrument such as an OSA or OCM in which no TE cooler is used.

The packaging described briefly above and in more detail below is suitable for any of a variety of free-space filters, such as TTFF, micro-electromechanical systems (MEMS) based Fabry-Perot filters, holographic or grating filters and piezo-electric Fabry-Perot based filters.

Hermetic packages of the type disclosed herein are desirable for optical components due to the strict reliability requirements of optical communications systems. Current hermetic multi-port optical device packaging technologies include butterfly, miniDIL, and innumerous machined aluminum packages. To maintain hermeticity, virtually all packages used for pass through optics employ laser welding for seam sealing, which is both complex and expensive to implement in production. The simplest packages of this type often cost upwards of $20.00 each, while the more complex can approach hundreds of dollars.

Figure 26A:
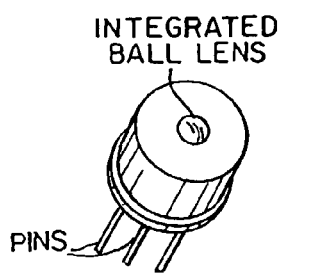
FIG. 26 is a perspective view of three TO packages having different fiber connection ports in the tops thereof.
Figure 26B:
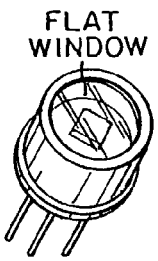
Figure 26C:
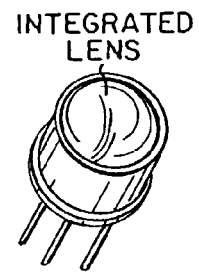
Figure 27:
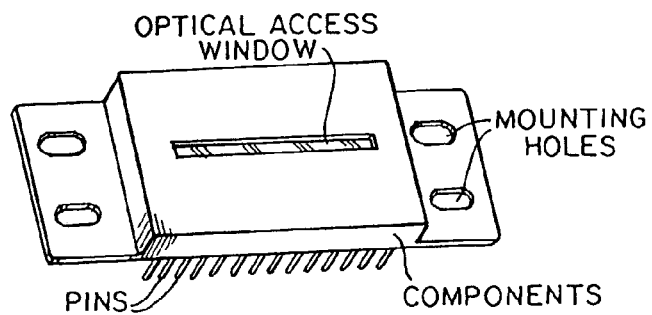
FIG. 27 is a perspective view of a dual in line pin (DIP) package with an optical port in the top thereof.

Other package styles are also available. Packaging used to house the optoelectronic assembly may include, but are not limited to TO type packages with front window of type used for single detectors as shown in FIG. 26; and dual-inline packages with front window of type used for linear detector arrays as shown in FIG. 27.

Preferred embodiments include low-cost assemblies to align and hold the active optoelectronic components inside the package. The components are stacked on top of each other under the package window while providing for low-cost assembly, proper thermal management, and good electrical contacts. Specifically, we use a "stand-off" element made out of an electrically insulating material such as a ceramic, for example, alumina or aluminum nitride. This element is used to suspend the tunable filter a fixed, well-controlled distance above the detector or emitter element. Additionally, conductive traces or contact pads may be defined on this stand-off for the purpose of contacting and interconnect. Using passive alignment guides or reference marks, optoelectronic components may be accurately aligned in the x-y plane, and accurately placed along the z-axis. Typical requirements for free-space elements is on the order of 10 microns. Such assembly, which may be accomplished using standard chip-mounting equipment, and possibly done in large volumes on an automated line is dramatically more cost-effective than "silicon micro-bench" type assemblies typically used for multi-element optical communications assemblies. In addition, it is significantly more resilient mechanically because all components lay flat on the stand-off or package surfaces.

Z-axis buildup methods are low cost, including but not limited to:
Multilevel (stepped) standoffs such as ceramics used to space apart components along z-axis and align them on the x-y plane;
Flip-chip mounting of optical/optoelectronic and other chips onto passive substrates and/or substrates on which other optoelectronic elements are fabricated;
Pre-mounting of components onto substrates/standoffs and assembly into package using passive alignment of these substrates; and
Mounting of substrates or components directly into electrical pins inside the package.

Figure 28:
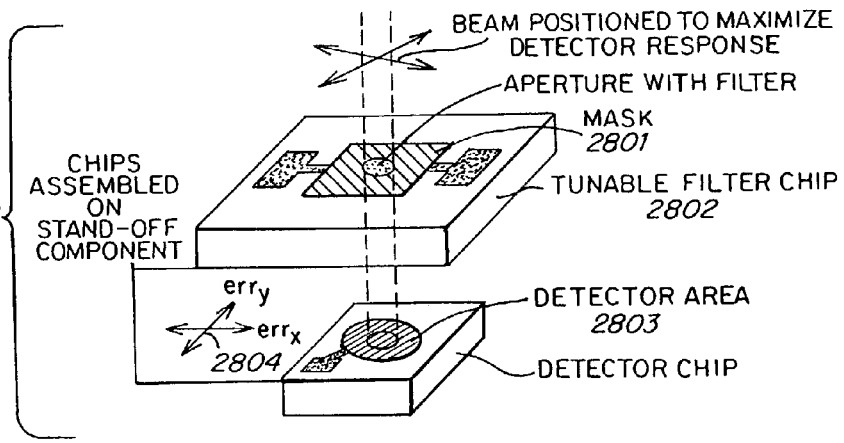
FIG. 28 is a perspective exploded view of a mask alignment system for assembling an optical component.
Figure 29:
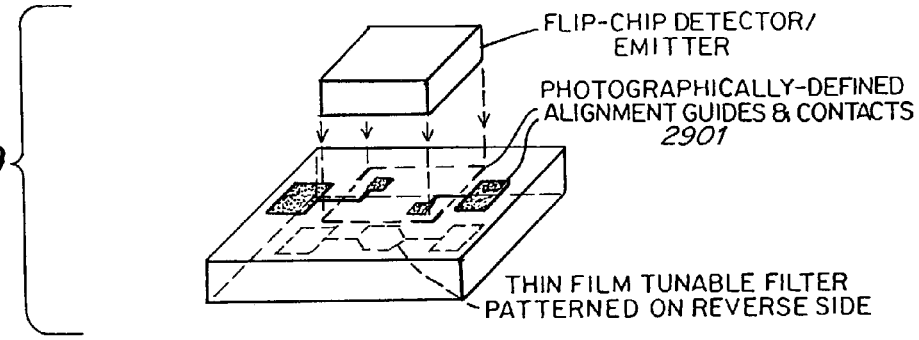
FIG. 29 is a perspective exploded view of a surface mount technology (SMT) alignment system for assembling an optical component.
Figure 30:
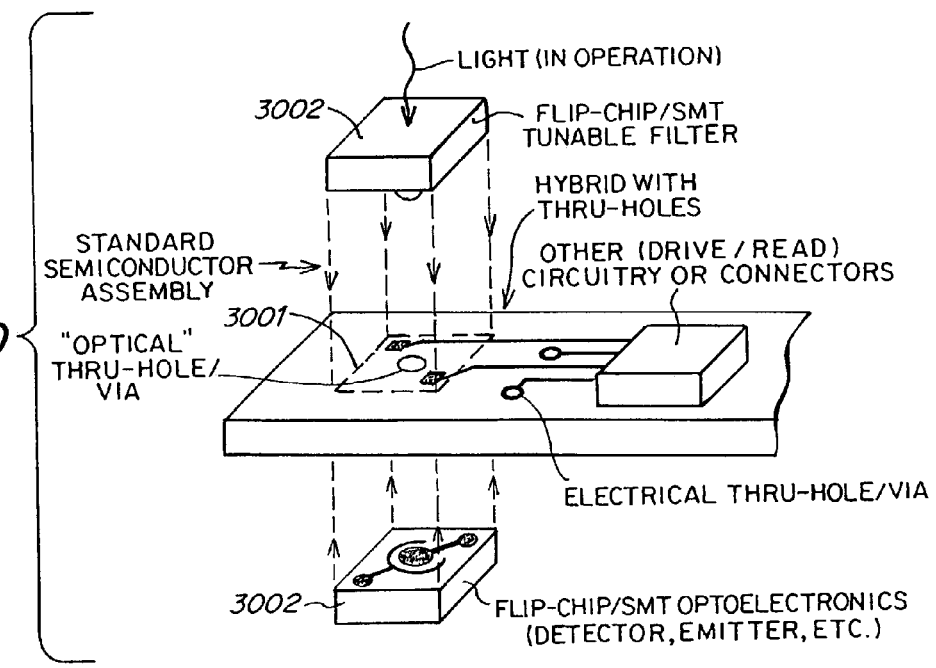
FIG. 30 is a perspective exploded view of an intermediate mask alignment system for assembling an optical component.

Several patterning methods may be used to minimize the assembly precision and effort required. These include but are not limited to:
(a) Patterning a mask 2801 or aperture on one component, such as the tunable filter 2802, and using other components that have a significantly larger active area 2803 enough to account for passive alignment tolerances 2804 as shown in FIG. 28;
(b) Using standardized surface-mount technology (SMT) assembly methods and machines to obtain high alignment accuracies, possibly the aid of optical alignment guides 2901 that are interpreted by SMT machinery as shown in FIG. 29; and
(c) Use of intermediate masks on substrates or optics to align individual optical/optoelectronic components 3002 as shown in FIG. 30.

Figure 31:
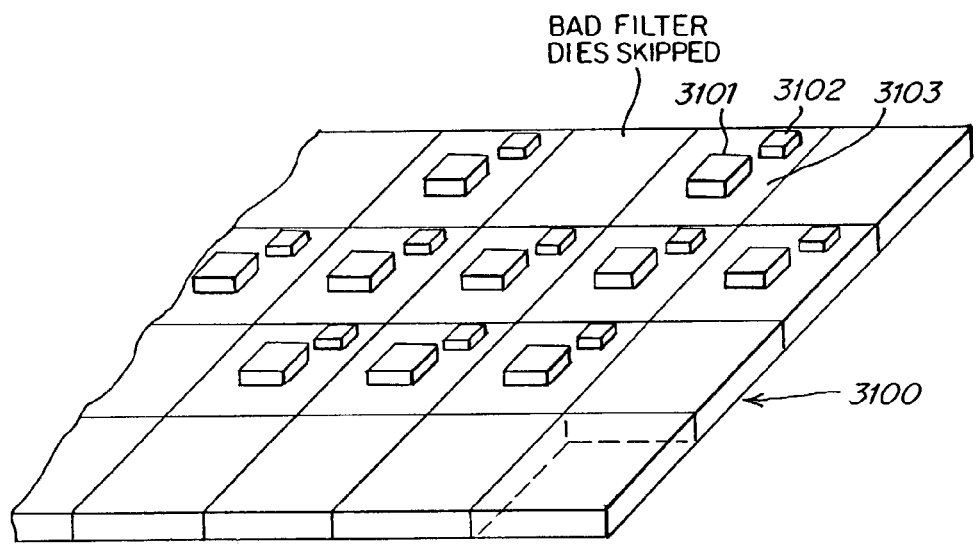
FIG. 31 is a perspective view showing multiple die assembly in a large sheet.
Figure 32:
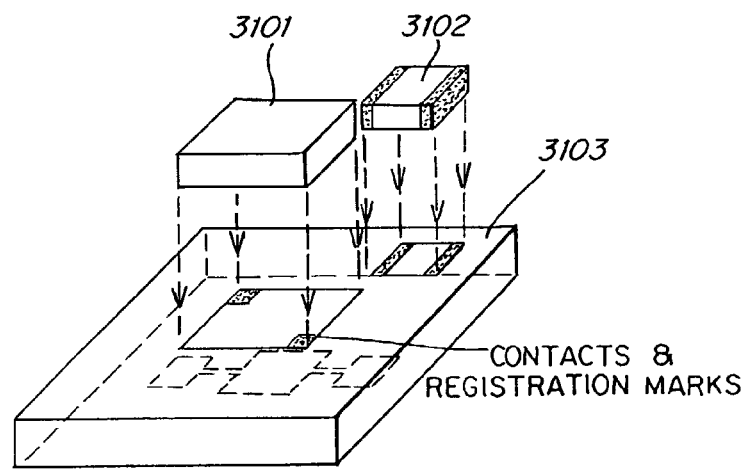
FIG. 32 is a perspective view showing a separated die from the sheet shown in FIG. 31.

Large-volume assembly of components based on conventional electronics methods, SMT for instance, may be used to build optoelectronic assemblies in "sheets" 3100 before dicing and packaging them. An example of such an assembly process is shown in FIG. 31, where a detector 3101 and thermistor element 3102 are mounted on the reverse side of a tunable thin film filter substrate. Several hundred or thousand such subassemblies may be automatically assembled and a solder reflow or wirebond process performed before the thin film filter wafer is diced and the resulting subassemblies are packaged. FIG. 32 shows one method of building such assemblies. A single substrate is patterned to accept the detector, filter, and possibly other components and is then diced; certain pieces of the substrate are then stacked to create stand-off elements with patterned metal traces.

The optical configurations that may be used with such a package include but are not limited to:
Inbound only, outbound only, or both in- and outbound optical signals Collimated or focused beams External optics only, combination of external and internal optics, or internal/package-integrated optics only;

Passive optical coatings used on external optics, on the transparent window to the package, or on internal elements such as substrates for the purpose of anti-reflection coatings, high-reflection coatings, or selective wavelength filtering;

Such optics may include elements such as single- or dual-fiber collimators used external to the package, lenses integrated into the package itself, or micro-optical elements used in the stack-up of components internal to the package.

Figure 34:
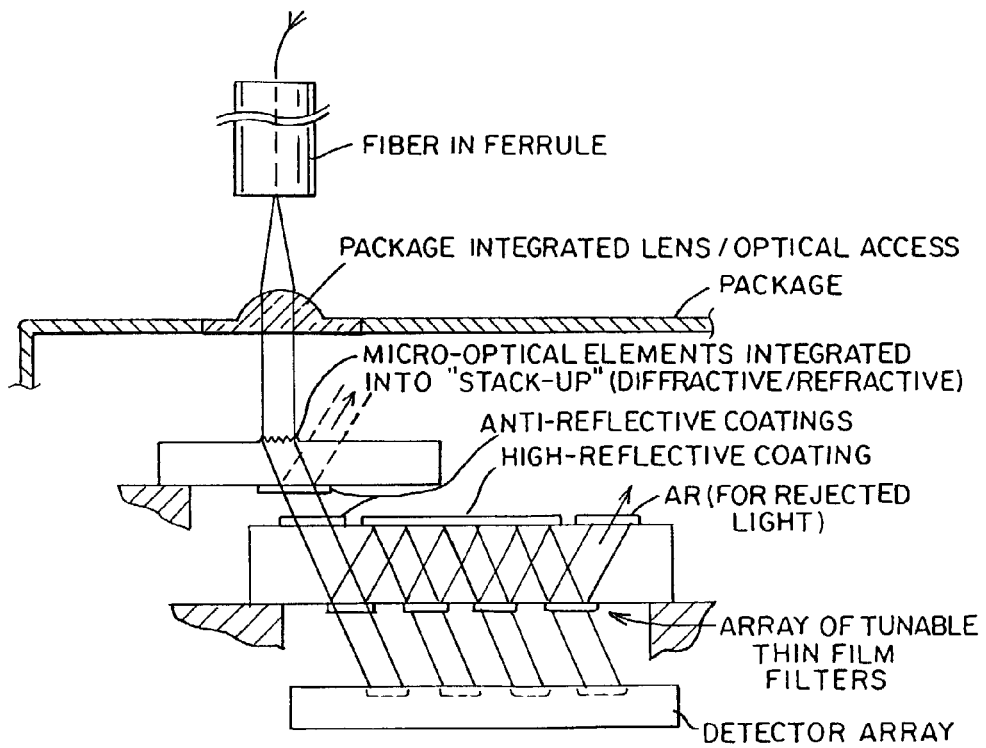
FIG. 34 is a cross section view of an optical assembly including a bare fiber that introduces light through a collimating lens and diffraction grating that directs light onto an array of filters and detectors.
Figure 35:
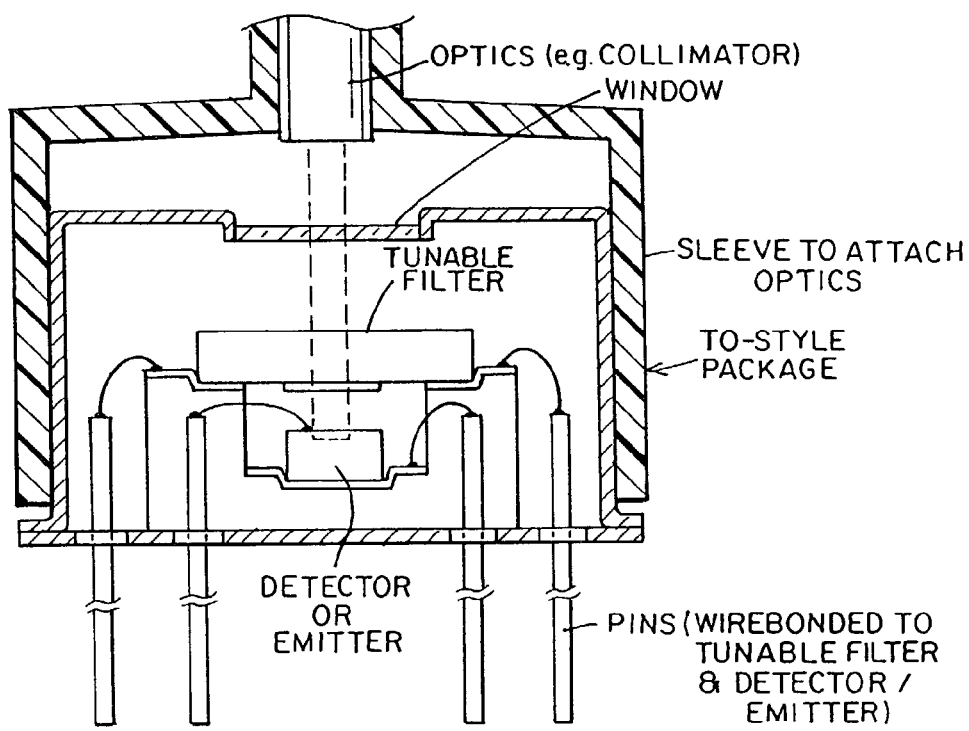
FIG. 35 is a cross section view of a TO package with a ferrule to receive a fiber.

FIGS. 33 and 34 show two examples of such optical assemblies. FIG. 33 shows a dual-fiber collimator used external to the package to introduce light into the package through the optical access port where it is filtered by a free space tunable filter. The reflected i.e., rejected, light is collimated into an output fiber. The remaining light, in the filter's pass band, passes through the filter substrate which is mounted on a stand-off and hits a detector mounted directly under it. This design minimizes the optics required within the optoelectronics package and significantly reduces the accuracy with which it must be assembled. FIG. 35 shows a bare fiber, in a ferrule, is used to introduce light, through a lens which is integrated with the package and acts as a collimator, into the package. Here, the light is deflected to an angle by a diffractive optical element and routed into an optical chip which has patterned on it multiple optical coatings including anti-reflective coatings at the input and "reject" ports, high-reflective coatings, either dielectric or metallic, in order to maintain light within the chip, and a series of tunable thin film filters which may be independently tuned. Finally, a detector array is used underneath the tunable filters to convert the optical signals into electronic ones.

Figure 36:
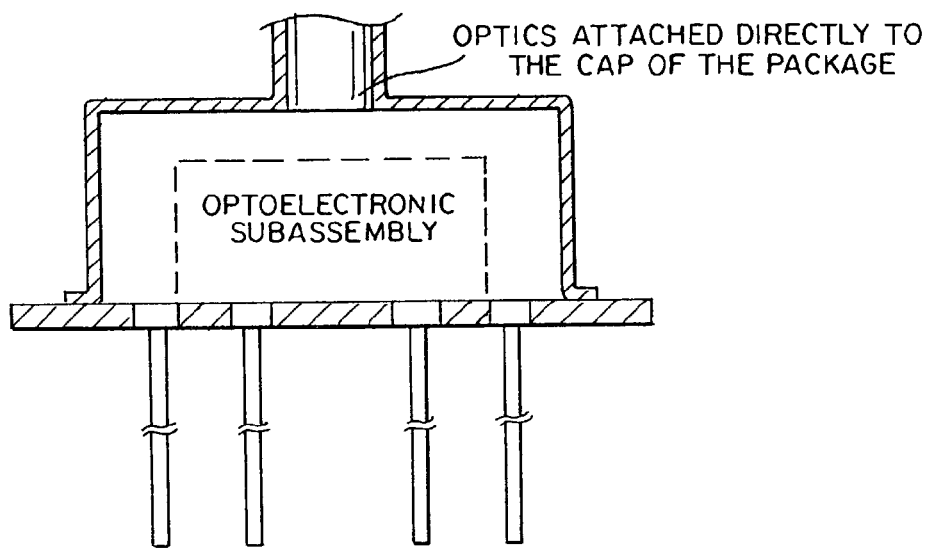
FIG. 36 is a cross section view of a TO package with a direct mount in the cap for receiving a fiber.
Figure 37:
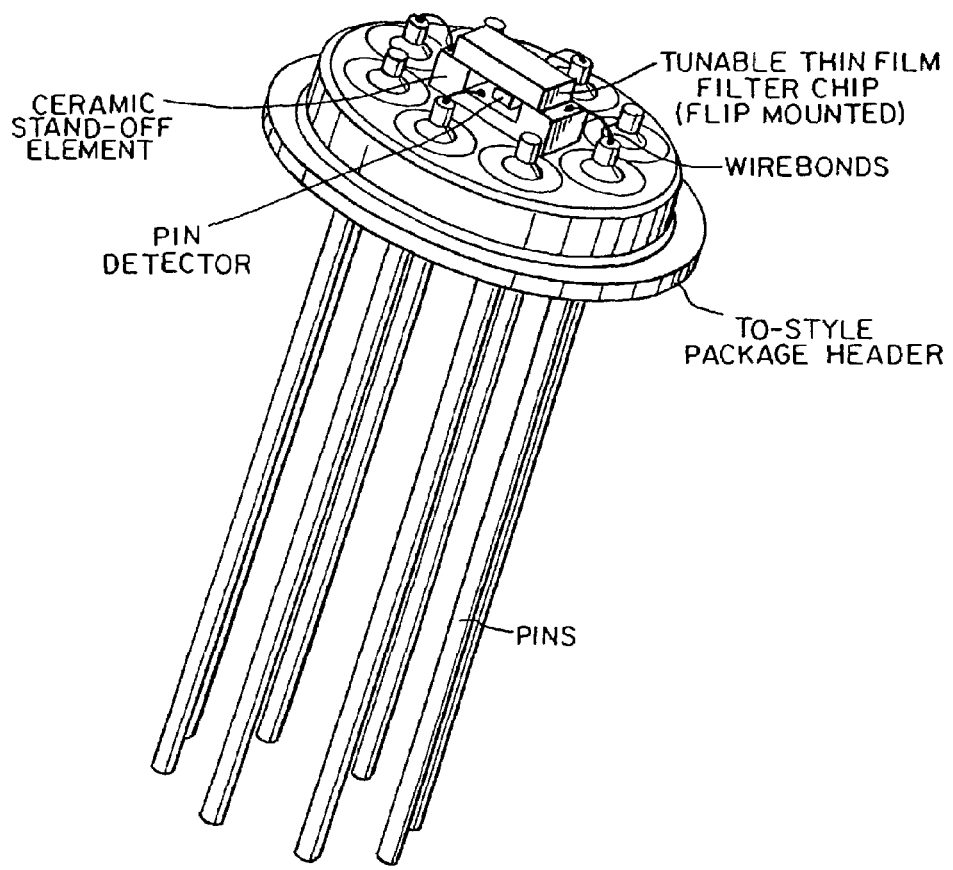
FIG. 37 is a perspective view of a TO header to which an optical component has been mounted and bonded for electrical connection.

FIG. 35 shows an example of a tunable thin film filter integrated with an InGaAs detector. The design utilizes a metallized ceramic stand-off element which acts both (1) to position the tunable thin film filter over the detector and (2) to allow contacting to the flip-mounted tunable thin film filter and detector simultaneously. Note that flip chipping is not a requirement, and that contacts can be made directly to the top side using wirebonding. FIG. 36 shows the subassembly on the header, before the package cap and collimator are attached. Note that the collimator could be attached directly to the package cap to eliminate one element and assembly step, as shown in FIG. 37. This package is used as the optoelectronic portion of a miniature optical spectrum analyzer, where the tunable filter is used to scan a wavelength range and the detector records optical power at each wavelength, which is described above.

There may be a broad range of applications that require similar systems, where the active optical elements besides the tunable filter are detectors, emitters, or other optical elements used to measure or treat light. The foregoing aspects of embodiments of the invention permit such to be constructed in a low-cost, small form factor manner to make their widespread application feasible.

The present invention has now been described in connection with a number of specific embodiments thereof. However, numerous modifications, which are contemplated as falling within the scope of the present invention, should now be apparent to those skilled in the art. Therefore, it is intended that the scope of the present invention be limited only by the scope of the claims appended hereto.

What is claimed is:

1. An optical instrument comprising:
    a thermo-optically tunable, thin film, free-space interference filter having a tunable passband which functions as a wavelength selector, said filter comprising a sequence of alternating layers of amorphous silicon and a dielectric material deposited one on top of the other, said sequence of alternating layers forming a Fabry-Perot cavity structure including: a first multi-layer thin film interference structure forming a first mirror; a thin-film spacer layer deposited on a top surface of the first multi-layer thin-film interference structure, said thin-film spacer layer made of amorphous silicon; and a second multi-layer thin film interference structure deposited on a top surface of the thin-film spacer layer and forming a second mirror;
    a lens for coupling an optical beam into the filter;
    an optical detector for receiving the optical beam after the optical beam has interacted with the interference filter; and
    circuitry for heating the thermo-optically tunable interference filter to control a location of the passband.

2. The optical instrument of claim 1, wherein the optical instrument is an optical spectrum analyzer.

3. The optical instrument of claim 2, wherein the optical spectrum analyzer is constructed and arranged as an optical channel monitor for wavelength-division multiplexed optical communication systems.

4. The optical instrument of claim 1, wherein the transparent layer is a transparent conducting oxide.

5. The optical instrument of claim 1, wherein the dielectric material is silicon nitride.

6. The optical instrument of claim 5, wherein the filter has a multi-cavity structure.

7. The optical instrument of claim 5, further comprising a single hermetic package, wherein the filter and the optical detector are mounted in the single hermetic package.

8. The optical instrument of claim 7, wherein the single hermetic package is a transistor outline (TO-style) package.

9. The optical instrument of claim 7, further comprising within the single hermetic package one or more discrete temperature sensors.

10. The optical instrument of claim 7, further comprising within the single hermetic package one or more temperature-stabilizing devices.

11. The optical instrument of claim 5, further comprising a device that measures temperature of the thermo-optically tunable filter to determine wavelength.

12. The optical instrument of claim 11, wherein the device that measures the temperature is integrated with the filter.

13. The optical instrument of claim 5, further comprising a signal processor connected to receive an output signal from the detector, the signal processor converting the output signal received from the detector to power v. wavelength data.

14. The optical instrument of claim 5, further comprising an electronics module;
    a fiber optic input; and
    a transistor outline (TO) package into which are mounted the tunable free-space filter, the optical detector and the fiber optic input, the TO package including pins through which electrical connections between the tunable free-space filter and the optical detector, and the electronics module are made.

15. The optical instrument of claim 5, wherein the filter further comprises a layer of electrically resistive material to which, during use, power is supplied by said circuitry to change the temperature of the filter and thereby shift the passband of the filter.

16. The optical instrument of claim 15, wherein the filter further comprises a substrate on which the first multi-layer thin film interference structure is deposited, wherein said layer of electrically resistive material forms a ring heater on the substrate and circumscribing an optical path through the first and second Fabry-Perot cavity structures, wherein during use the power that is supplied to the ring heater by said circuitry is electrical power.

17. The optical instrument of claim 15, wherein the filter further comprises a crystalline semiconductor substrate on which the first multi-layer thin film interference structure is deposited, wherein said layer of electrically resistive material is a doped upper region of said substrate, wherein during use the power that is supplied to the doped upper region by said circuitry is electrical power.

18. The optical instrument of claim 15, wherein the filter further comprises a substrate and a heater film formed in the substrate, wherein the first multi-layer thin film interference structure is deposited on the heater film, wherein said layer of electrically resistive material is said heater film and wherein during use the power that is supplied to the heater film by said circuitry is electrical power.

19. The optical instrument of claim 15, wherein said layer of electrically resistive material is one of the layers of the Fabry-Perot cavity structure.

20. The optical instrument of claim 15, wherein said layer of electrically resistive material is an optically transparent layer that is integrated with the filter in a location such that light passes through the electrically resistive material.

* * * * *